United States Patent
Sasa et al.

(10) Patent No.: US 7,440,605 B2
(45) Date of Patent: Oct. 21, 2008

(54) DEFECT INSPECTION APPARATUS, DEFECT INSPECTION METHOD AND PROGRAM

(75) Inventors: Yasushi Sasa, Kyoto (JP); Hiroyuki Onishi, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 632 days.

(21) Appl. No.: 10/657,107

(22) Filed: Sep. 9, 2003

(65) Prior Publication Data

US 2004/0066962 A1     Apr. 8, 2004

(30) Foreign Application Priority Data

Oct. 8, 2002     (JP)     ............... P2002-294851

(51) Int. Cl.
*G06K 9/00*     (2006.01)
(52) U.S. Cl. ............................................ 382/141
(58) Field of Classification Search ............... None
See application file for complete search history.

(56) References Cited

U.S. PATENT DOCUMENTS

| | | | |
|---|---|---|---|
| 4,433,385 A * | 2/1984 | De Gasperi et al. | 382/149 |
| 5,600,734 A * | 2/1997 | Okubo et al. | 382/147 |
| 5,875,267 A * | 2/1999 | Djakovic | 382/263 |
| 5,946,406 A * | 8/1999 | Frink et al. | 382/119 |
| 6,169,282 B1 | 1/2001 | Maeda et al. | |
| 6,437,862 B1 | 8/2002 | Miyazaki et al. | |
| 7,116,816 B2 * | 10/2006 | Tanaka et al. | 382/149 |

FOREIGN PATENT DOCUMENTS

| | | |
|---|---|---|
| JP | 04-107945 | 4/1992 |
| JP | 07-027711 | 1/1995 |

(Continued)

OTHER PUBLICATIONS

Nobuyuki Otsu "An Automatic Threshold Selection Method Based on Discriminant and Least Squares Criteria" IEICE, '80/4 vol. J63-D, No. 4, pp. 349-356 (with English translation f the abstract).

(Continued)

*Primary Examiner*—Matthew C Bella
*Assistant Examiner*—Alex Liew
(74) *Attorney, Agent, or Firm*—McDermott Will & Emery LLP

(57) ABSTRACT

A reference image and an inspection image indicating pattern on a substrate are acquired and a specified pixel value range (63) is set on the basis of a histogram (62a) of pixel values of the reference image. Then, a transfer curve (71) having a large inclination in the specified pixel value range (63) is obtained. The inspection image and the reference image are converted in accordance with an LUT having transfer characteristics indicated by the transfer curve (71), an enhanced differential image between a converted inspection image and a converted reference image is generated and each pixel value of the enhanced differential image is compared with a predetermined threshold value, to thereby perform a detection of defective pixel. With this, a value of pixel in the enhanced differential image which corresponds to a pixel in the reference image (or inspection image) having the pixel value in the specified pixel value range (63) is enhanced, and appropriate inspection is thereby performed.

25 Claims, 23 Drawing Sheets

FOREIGN PATENT DOCUMENTS

| JP | 9-127008 | 5/1997 |
|---|---|---|
| JP | 09-236487 | 9/1997 |
| JP | 11-132959 | 5/1999 |
| JP | 2001-4347 | 1/2001 |
| JP | 2002-022421 | 1/2002 |

OTHER PUBLICATIONS

Nobuyuki Otsu "A Threshold Selection Method from Gray-Level Histograms" IEEE Transactions on Systems, Man, and Cybernetics, 79/1 vol. SMC-9, No. 1, pp. 62-66.

Japanese Office Action issued in corresponding Japanese Patent Application No. JP 2002-294851, dated Apr. 18, 2007.

Japanese Office Action issued in Japanese Patent Application No. JP 2002-294851, mailed Sep. 19, 2007.

Japanese Office Action issued in Japanese Patent Application No. JP 2002-294851, mailed May 13, 2008.

* cited by examiner

Background Art

DEFECT INSPECTION APPARATUS, DEFECT INSPECTION METHOD AND PROGRAM

BACKGROUND OF THE INVENTION

1. Field of the Invention

The present invention relates to a technique for inspecting pattern on an object.

2. Description of the Background Art

In the field of appearance inspection of pattern formed on a semiconductor substrate, a color filter, a shadow mask, a high-definition printed circuit board or the like, pattern of lead frame, pattern of photomask used for forming these patterns or the like, conventionally, a comparison check method has been mainly performed with multitone images. For example, a differential absolute value image which indicates absolute values of the difference in pixel between an inspection image (an image to be inspected) and a reference image is obtained and a region in the differential absolute value image which has pixel values larger than a predetermined threshold value is detected as a defect.

In the comparison check method, since it is premised that conditions such as dynamic range and brightness of the inspection image and the reference image are equal, in order to remove an effect of variation in dynamic range, brightness and the like, also performed is a method of detecting defects after normalizing a pixel value distribution by linear transformation so that pixel values of an image should be appropriately distributed in a predetermined range.

As disclosed in Japanese Patent Application Laid Open Gazette No. 2002-22421, proposed is a method of removing an effect of variation in sharpness of image (in other words, variation in graininess) by calculating a standard deviation of signed difference in pixel value between the inspection image and the reference image and normalizing a histogram of the differential absolute value image on the basis of the standard deviation.

In some cases, the pixel value becomes as large as that in a defective portion in some region of the differential absolute value image due to an effect of a surface state of an object to be picked up or an image pickup part (such as a charge-up phenomenon which is found in an image picked up by using an electron beam like an SEM) and the like. An unnecessary increase in pixel value of the differential absolute value image is caused, in many cases, in an extremely local region consisting of several pixels, and in such a case, it is impossible to appropriately detect a defect by correction of pixel value in a conventional macroscopic method.

In a case where, for example, dynamic ranges of the inspection image and the reference image are matched with each other in a region consisting of about 100×100 pixels, an effect of variation in pixel value produced entirely on this region can be removed but the variation in pixel value caused by the charge-up phenomenon and the like in the region consisting of several pixels is still incorrectly detected as a defect.

FIG. 1 is a view showing incorrect detection of a defect due to the charge-up phenomenon. In FIG. 1, assuming that ideal values of pixel in a line 911 of an inspection image 91 (e.g., values of an reference image) are shown in graph 921 and actual pixel values are shown in graph 922, pixel values of the differential absolute value image are shown in graph 923.

As indicated by reference sign 922a in graph 922, when the pixel value is deviated from the ideal value due to a defect, the pixel value of the differential absolute value image becomes larger as indicated by reference sign 923a in graph 923, and this allows detection of the defect. When values of several pixels are deviated from the ideal value as indicated by reference sign 922b in graph 922, however, a defect is incorrectly detected as indicated by reference sign 923b in graph 923. Such a local wrong detection can not be avoided by the conventional method.

SUMMARY OF THE INVENTION

It is an object of the present invention to provide a technique for more appropriately detecting a defect on an object.

The present invention is intended for a defect inspection apparatus for inspecting pattern on an object. The defect inspection apparatus comprises an image pickup device for performing an image pickup of an object to acquire data of an inspection image which is multitone; a memory for storing data of a reference image; and an operation part for obtaining transfer characteristics to enhance difference between arbitrary pixels among a plurality of specified pixel values which are specified in defect detection and then obtaining an enhanced differential image between the inspection image and the reference image on the basis of the transfer characteristics, to perform inspection on the basis of the enhanced differential image.

In this present invention, by using the enhanced differential image, it is possible to perform appropriate inspection with attention to the specified pixel values. Especially, by setting a plurality of specified pixel values in accordance with the kind of defect to be detected, the inspection can be performed with high precision.

According to one preferred embodiment of the present invention, the transfer characteristics is set on the basis of pixel values of the inspection image or the reference image, and the operation part converts the inspection image and the reference image on the basis of the transfer characteristics to obtain a differential image between a converted inspection image and a converted reference image as the enhanced differential image.

The plurality of specified pixel values may be positioned outside a pixel value range corresponding to a specific region in the inspection image or the reference image. This makes it possible to detect a defect that the pixel value becomes extremely large or small.

The transfer characteristics may include inspection image transfer characteristics obtained from the inspection image and reference image transfer characteristics obtained from the reference image. In other words, the transfer characteristics may be obtained individually as the inspection image transfer characteristics and the reference image transfer characteristics or obtained as a synthesis of the inspection image transfer characteristics and the reference image transfer characteristics.

The operation part may synthesize a differential image between the inspection image and the reference image and the enhanced differential image and compare values of pixels in a synthesized image with a predetermined threshold value, to perform inspection. This makes it possible to relieve the degree of enhancement.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
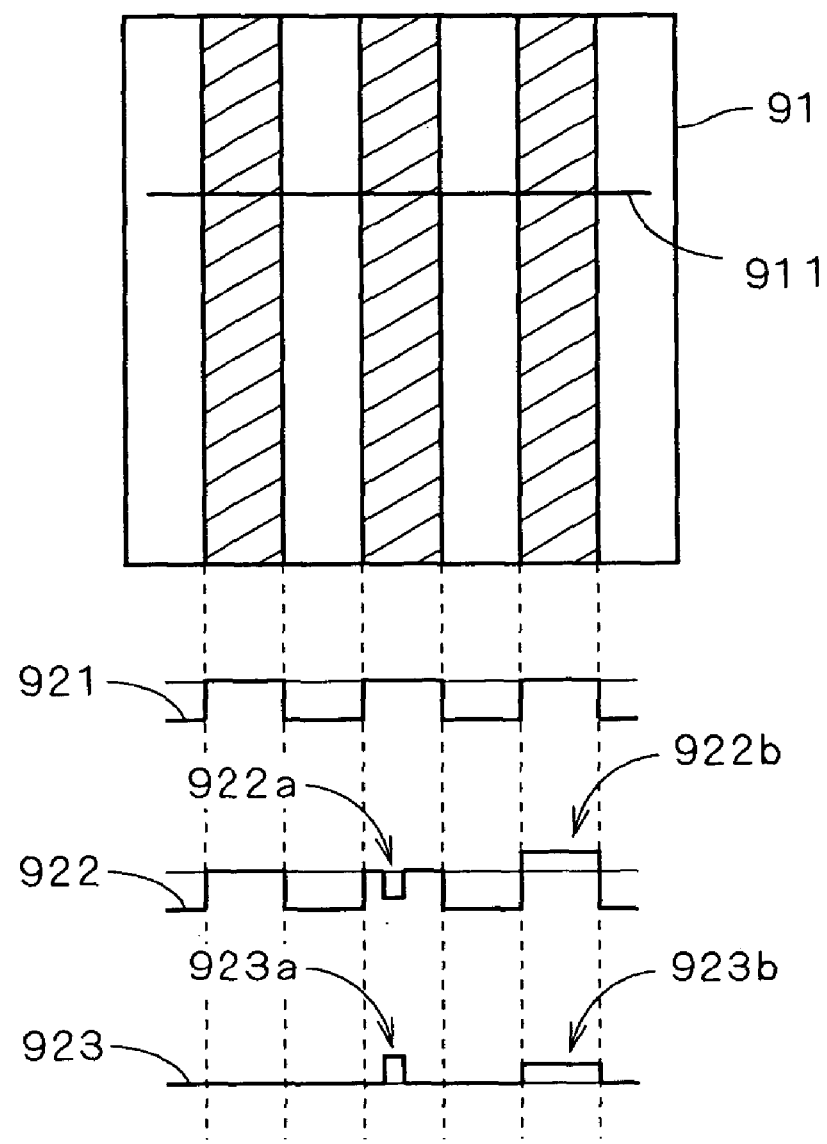
FIG. 1 is a view showing incorrect detection of a defect.
Figure 2:
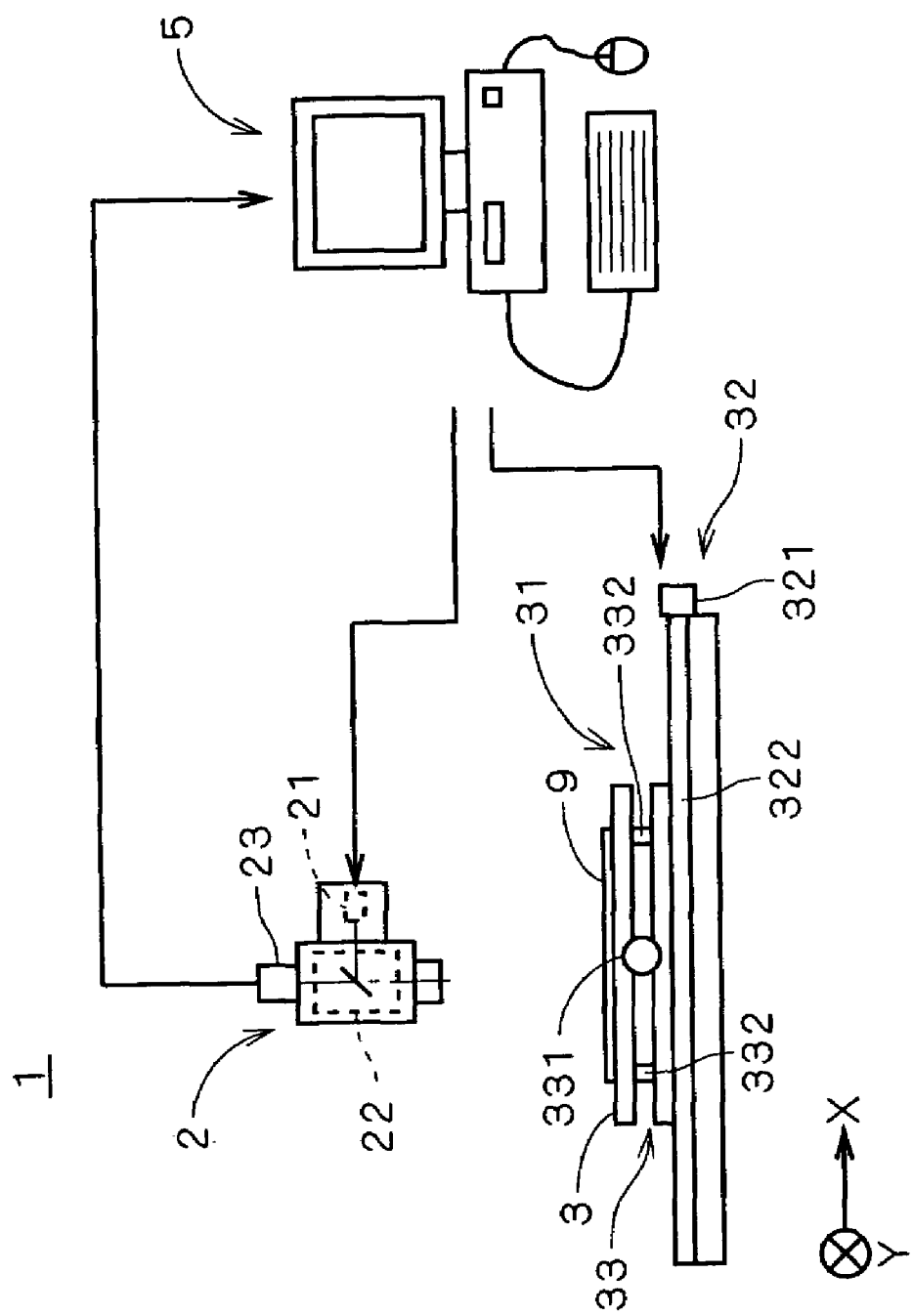
FIG. 2 is a diagram showing a construction of an inspection apparatus.

FIG. 2 is a view showing a construction of an inspection apparatus 1 in accordance with the preferred embodiment of the present invention. The inspection apparatus 1 is an apparatus for inspecting pattern on a semiconductor substrate (hereinafter, referred to as "substrate") 9 and comprises an image pickup part 2 for performing an image pickup of a predetermined region on the substrate 9 to acquire data of a multitone object image, a stage 3 for holding the substrate 9 and a stage driving part 31 for moving the stage 3 relatively to the image pickup part 2.

The image pickup part 2 comprises a lighting part 21 for emitting an illumination light, an optical system 22 for guiding the illumination light to the substrate 9 and receiving the light from the substrate 9 and an image pickup device 23 for converting an image of the substrate 9 formed by the optical system 22 into an electrical signal. This image pickup part 2 may be an image pick-up device using an electron beam. The stage driving part 31 has an X-direction moving mechanism 32 for moving the stage 3 in the X direction of FIG. 2 and a Y-direction moving mechanism 33 for moving the stage 3 in the Y direction. The X-direction moving mechanism 32 has a construction in which a ball screw (not shown) is connected to a motor 321 and moving the Y-direction moving mechanism 33 in the X direction of FIG. 2 along guide rails 322 with rotation of the motor 321. The Y-direction moving mechanism 33 has the same construction as the X-direction moving mechanism 32 and moves the stage 3 in the Y direction along guide rails 332 by its ball screw (not shown) with rotation of its motor 331.

The inspection apparatus 1 further comprises a computer 5 constituted of a CPU which performs various computations, memories which store various information and the like. The computer 5 performs a detection of defect and also serves as a control part which controls other constituent elements in the inspection apparatus 1.

Figure 3:
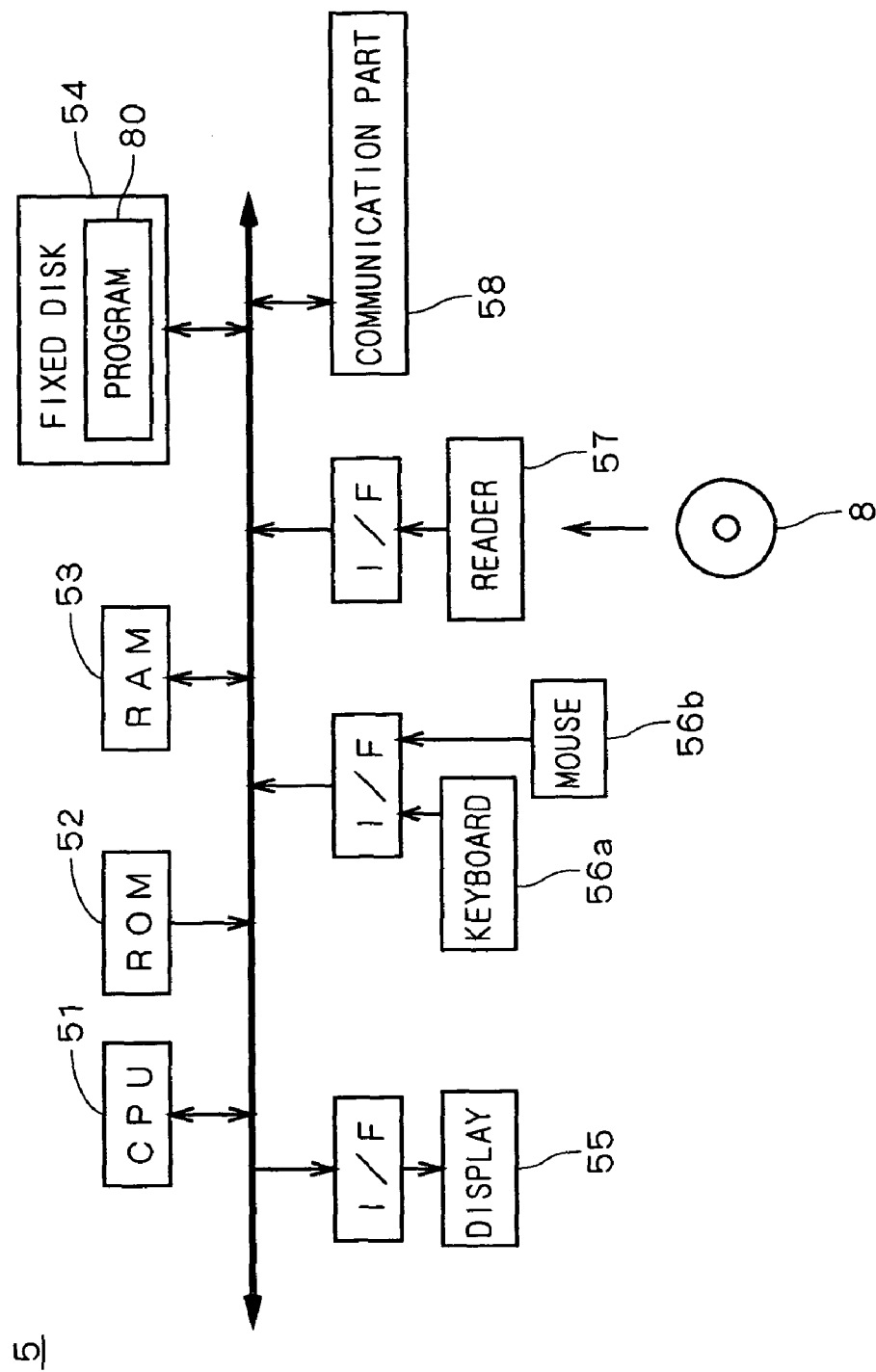
FIG. 3 is a block diagram showing a structure of a computer.

FIG. 3 is a block diagram showing a structure of the computer 5. The computer 5 has a constitution of general computer system where a CPU 51 for performing various computations, a ROM 52 for storing a basic program and a RAM 53 for storing various information are connected to a bus line. To the bus line, a fixed disk 54 for storing information, a display 55 for displaying various information such as images, a keyboard 56a and a mouse 56b for receiving an input from a user, a reader 57 for reading information from a computer-readable recording medium 8 such as an optical disk, a magnetic disk or a magneto-optic disk, and a communication part 58 for transmitting and receiving a signal to/from other constituent elements in the inspection apparatus 1 are further connected through an interface (I/F) as appropriate.

A program 80 is read out from the recording medium 8 through the reader 57 into the computer 5 and stored into the fixed disk 54 in advance. The program 80 is copied to the RAM 53 and the CPU 51 executes computation in accordance with the program stored in the RAM 53 (in other words, the computer executes the program), and the computer 5 thereby performs an operation of defect detection.

Figure 4:
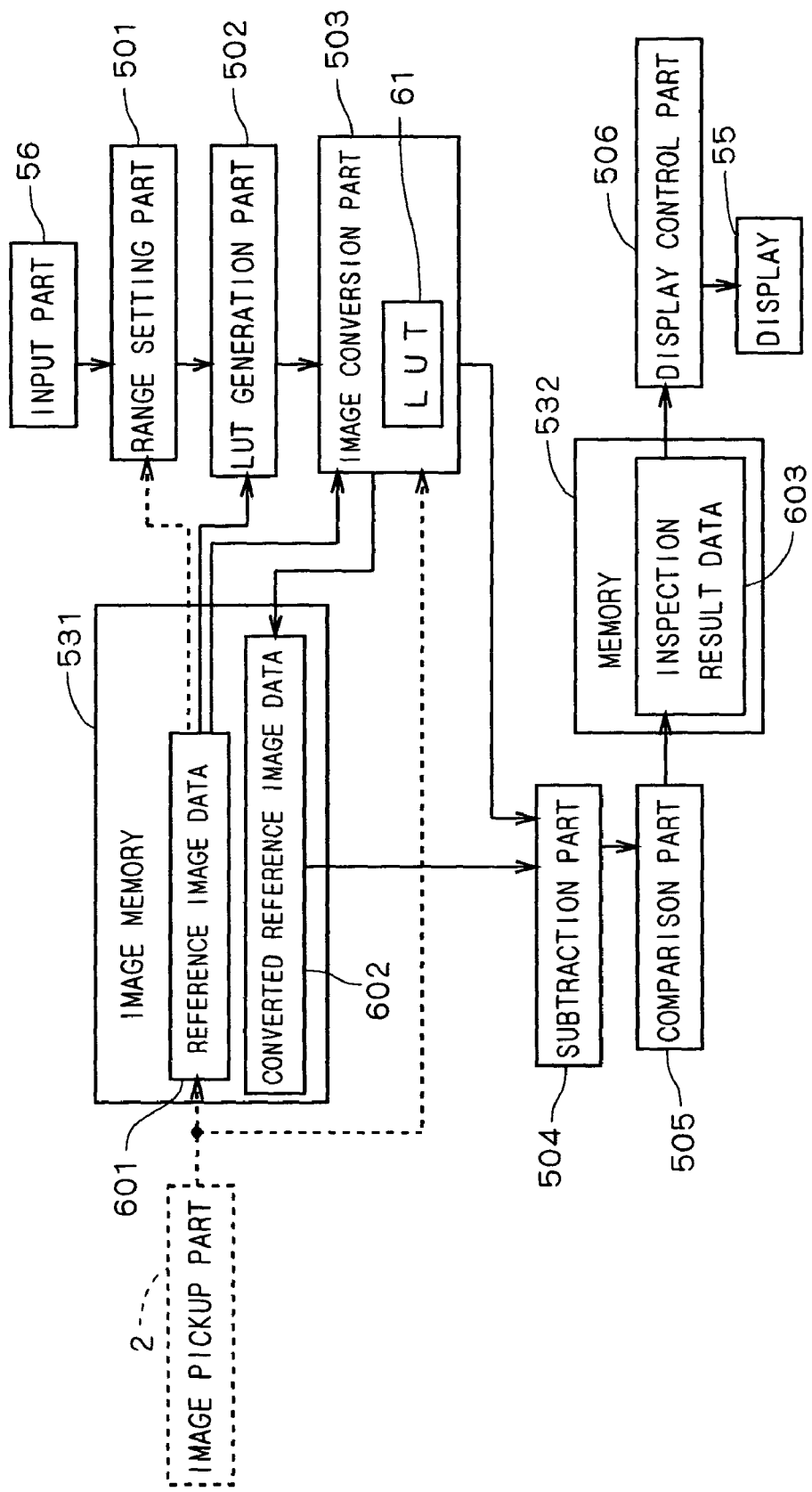
FIG. 4 is a diagram showing a functional structure of the computer.

FIG. 4 is a diagram showing a functional structure of the computer 5. In FIG. 4, an input part 56 corresponds to the keyboard 56a or the mouse 56b of FIG. 3 and an image memory 531 and a memory 532 correspond to the RAM 53 of FIG. 3. The image memory 531 may be a dedicated memory which is additionally provided in the computer 5.

A range setting part 501, an LUT (lookup table) generation part 502, an image conversion part 503, a subtraction part 504, a comparison part 505 and a display control part 506 represent functions performed by the CPU 51, the RAM 53 and other peripheral circuits when the CPU 51 performs a computation in accordance with the program 80. An operation of the inspection apparatus 1 will be discussed below, referring to FIGS. 2 to 4.

Figure 5:
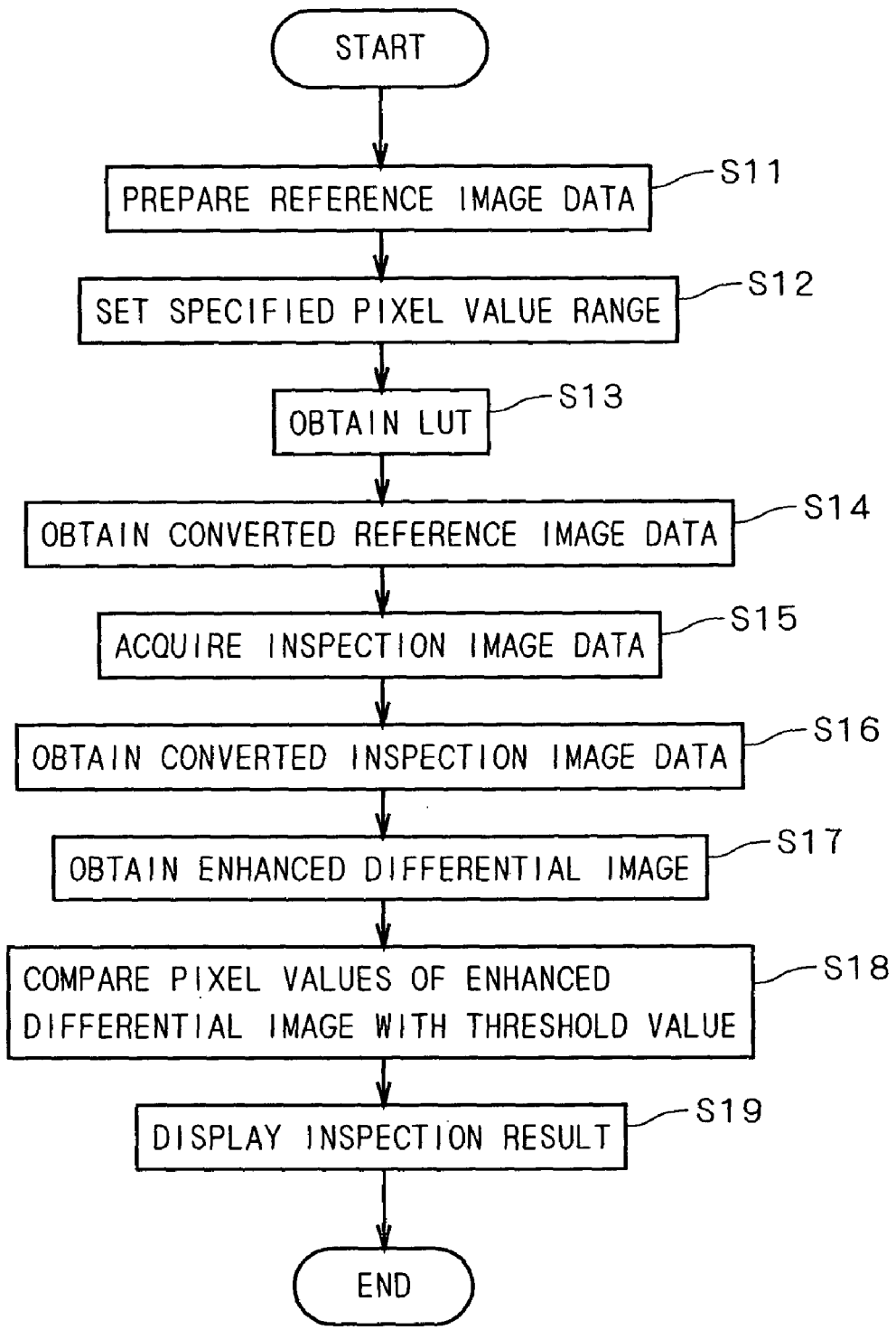
FIG. 5 is a flowchart showing an operation flow of the inspection apparatus.

FIG. 5 is a flowchart showing an operation flow of the inspection apparatus 1. In the inspection apparatus 1, first, the computer 5 controls the stage driving part 31 to relatively move an image pickup position corresponding to the image pickup part 2 to a predetermined position over the substrate 9 and the image pickup part 2 acquires data of object image of multitone (e.g., 256 tones if 8 bits). The image pickup (i.e., prescan) is performed for a region which is supposed to have no defect and the acquired data is stored in the image memory 531 and prepared as reference image data 601 (Step S1).

Next, the range setting part 501 sets a range of values of specified pixels in defect detection (hereinafter, referred to as a "specified pixel value range") (Step S12). The technical meaning of the specified pixel value range will be discussed later. It is selected in advance whether the setting of specified pixel value range is performed manually by a user or automatically.

Figure 6:
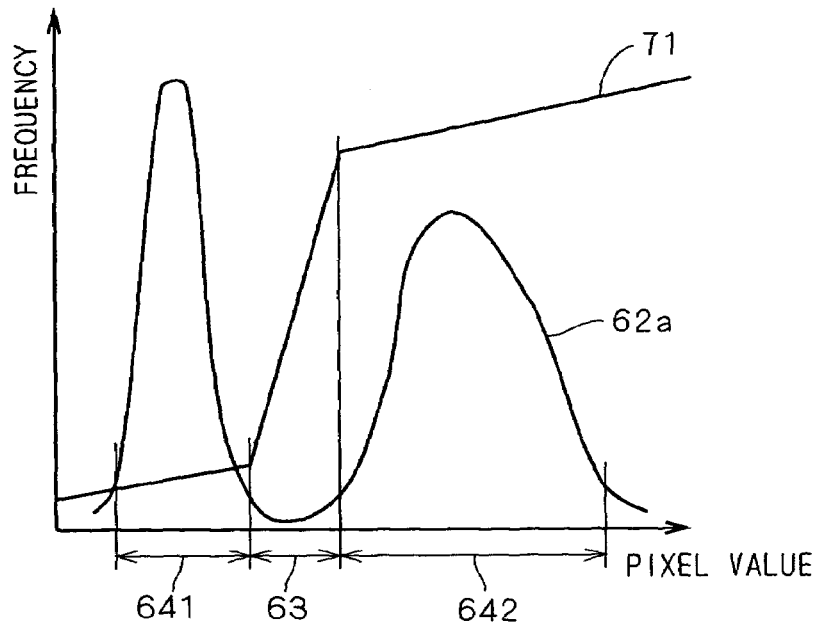
FIGS. 6 to 8 are graphs illustrating histograms and transfer curves.

When the setting of specified pixel value range is performed manually, first, the range setting part 501 acquires the reference image data 601, generates a histogram of pixel values of reference image and displays the histogram on the display 55. FIG. 6 is a graph illustrating a histogram 62a. When a histogram has two maximum values (this is hereinafter referred to as "bi-modality"), like the histogram 62a, a range near the center minimum value is set by the user as a specified pixel value range 63. The setting is performed by the range setting part 501 when the input part 56 receives the operation of the user. When the reference image has two kinds of regions (for example, a wiring pattern region and the other background region on the substrate 9), a range between respective ranges of pixel values which are supposed to be obtained from these regions is set as the specified pixel value range 63. In the manual setting, the specified pixel value range 63 is set in accordance with the intention of the user.

When the setting of specified pixel value range is performed automatically, for example, an average value around each of the peaks and a standard deviation σ of distribution around each of the peaks are obtained for the histogram 62a having bi-modality as shown in FIG. 6 and a range between ranges 641 and 642 each of which covers (±σ) of the corresponding peak centered at the average value of the peak is set as the specified pixel value range 63. The ranges 641 and 642 correspond to ranges of pixel values obtained from both the regions when the reference image has two kinds of regions. By using the standard deviation, it is possible to appropriately set the pixel value ranges corresponding to these regions.

Figure 7:
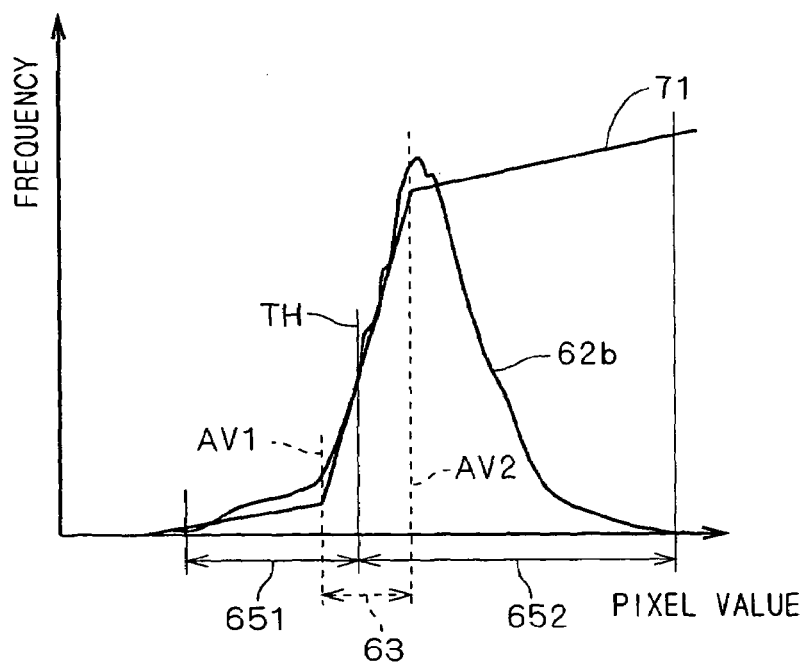

On the other hand, when a histogram does not have bi-modality like a histogram 62b (in other words, has a small contrast) as shown in FIG. 7, first, a threshold value TH is set and average values AV1 and AV2 of values of pixels belonging to predetermined ranges 651 and 652 on both sides of the threshold value TH are obtained. Then, a range between the average value AV1 and the average value AV2 is set as the specified pixel value range 63. When the reference image has two kinds of regions (for example, a wiring pattern region and the other background region on the substrate 9), the ranges 651 and 652 are ranges of pixel values which are supposed to be obtained from these regions. In other words, the average values AV1 and AV2 correspond to average values of values of the pixels belonging to these regions. Intermediate values or the like may be used instead of the average values AV1 and AV2.

As a method of setting a threshold value TH1, a method of setting a threshold value in binarization of a multivalued image or other various methods may be adopted. For example, a method disclosed in "An Automatic Threshold Selection Method Based on Discriminant and Least Squares Criteria" by Nobuyuki Otsu (IEICE (The Institute of Electronics, Information and Communication Engineers) Transactions, '80/4 vol. J63-D, No. 4, pp. 349-356) may be used. In this method, as a value for evaluation on propriety of a threshold value, measures of class separability based on within-class variance and between-class variance (herein, "class" refers to a group of pixel values which are divided by the threshold value) are adopted, and a threshold value is obtained so that the measures of class separability can be the maximum. By this method, even if a histogram of pixel values has no bi-modality when an image is divided into two regions, it is possible to steadily obtain an optimum threshold value in a non-parametric manner.

As a method of setting the threshold value TH, well known is Kittler's method where ambiguity which indicates which region (any one region among a plurality of regions of the reference image) an observed value (pixel value) belongs to is defined and a threshold value is set on the basis of a principle that the ambiguity is made minimum for the worst distribution (in other words, the normal distribution). Naturally, other various methods may be used as a method of setting the threshold value TH.

When the specified pixel value range 63 is set, next, the LUT generation part 502 obtains an LUT (lookup table) for converting the image (Step S13). Specifically, the LUT which corresponds to the transfer curve indicated by reference sign 71 in FIGS. 6 and 7 is obtained. An obtained LUT 61 is stored in the memory of the image conversion part 503 as shown in FIG. 4. For the transfer curve 71, the horizontal axis and the vertical axis correspond to pixel values. Specifically, in the transfer curve 71, a pixel value on the horizontal axis (e.g., any one value within a range from 0 to 255) is transferred to a pixel value on the vertical axis (this value may be a value within the range from 0 to 255 or in a broader range with more tones).

The inclination of the transfer curve 71 is made larger in the specified pixel value range 63 than in other pixel value ranges. As a result, by the transfer characteristics in accordance with the transfer curve 71, the difference between any two pixel values in the specified pixel value range 63 is enhanced (in other words, the difference between any two pixel values in the specified pixel value range 63 is enlarged relatively to the difference between the two pixel values in other pixel value ranges). When one of the pixel values is included in the specified pixel value range 63 and the other pixel value is not included in the specified pixel value range 63, the difference between the two pixel values is relatively enhanced to some degrees as compared with the case where both pixel values are not included in the specified pixel value range 63.

The image conversion part 503 transfers the pixel values of the reference image by using the LUT 61, generates a converted reference image and stores the converted reference image in the image memory 531 as converted reference image data 602 (Step S14). Through the above operations, preparation for inspection of pattern on the substrate 9 is completed.

Next, the inspection apparatus 1 moves a region on the substrate 9 to be inspected to a portion immediately below the image pickup part 2 to perform an image pickup and the image pickup part 2 acquires data of inspection image (i.e., image to be inspected) (Step S15). On the substrate 9, there are a plurality of blocks in which the same patterns are formed, and an image of specific pattern in one block is acquired as the reference image and an image of the same pattern (in other words, a region corresponding to the reference image) in other blocks is acquired as an inspection image.

The pixel values of the inspection image are subsequently inputted to the image conversion part 503, the value of each pixel of the inspection image is transferred in accordance with the LUT 61 and the result is outputted to the subtraction part 504. With this operation, data of converted inspection image is substantially obtained (Step S16).

At the same time when the pixel value of the converted inspection image is inputted to the subtraction part 504, the pixel value corresponding to the converted reference image is inputted from the image memory 531 and the subtraction part 504 obtains a differential absolute value between these pixel values. With this operation, the subtraction part 504 substantially obtains the differential absolute value image between the converted inspection image and the converted reference image (hereinafter, referred to as an "enhanced differential image") (Step S17).

The differential absolute value obtained by the subtraction part 504 is compared with a predetermined threshold value by the comparison part 505 (Step S18), and when the differential absolute value is smaller than the threshold value, it is determined that the corresponding pixel in the inspection image is not included in a defect and when the differential absolute value is larger than the threshold value, it is determined that the corresponding pixel in the inspection image is included in a defect. A set of comparison results corresponding to the whole inspection image is stored in the memory 532 as inspection result data 603. The inspection result data 603 is displayed as binary image on the display 55 through the display control part 506 if necessary (Step S19), and then the user confirms whether there is a defect or not.

Thus, in the inspection apparatus 1, the inspection image and the reference image are converted in accordance with the LUT 61 and inspection is performed by using the differential absolute value image between these images after conversion. Since the LUT 61 is used for such transfer (or conversion) as to enhance the difference between any two pixel values in the specified pixel value range, when a value of pixel at a position in the inspection image and a value of pixel corresponding to the reference image are included in the specified pixel value range, the difference between these pixel values is enhanced (relatively to the case where these pixel values are outside the specified pixel value range).

When the reference image has two kinds of regions, e.g., a wiring pattern region and the other background region on the substrate 9, since the specified pixel value range is positioned at least between representative values of the pixel values corresponding to these two regions (the most preferable representative value is an average value which is easily obtained) (though the specified pixel value range corresponds to a pixel value range between the pixel value ranges obtained from these two regions in the case of FIG. 6, this pixel value range is positioned between the representative values), the pixel value of the enhanced differential image is enhanced by transfer in accordance with the LUT 61, relatively to a pixel which is substantially uncertain on which one of the two kinds of regions it belongs to (or which has relatively small possibility of belonging to any one of the two regions).

Through the above operations, for example, by setting the specified pixel value range 63 so that the pixel values in the inspection image should not be included even if there is variation in pixel value caused by the charge-up phenomenon of the image pickup part 2 or the like, it is possible to make the pixel value in the enhanced differential image which corresponds to the charge-up phenomenon relatively smaller than the pixel value corresponding to by a defect. As a result, the difference in pixel value between the inspection image and the reference image which is caused by a defect can be enhanced and it becomes possible to appropriately detect a defect by comparing the pixel value in the enhanced differential image with the predetermined threshold value.

By setting a pixel value range between the representative values in the pixel value ranges obtained from two regions in the reference image as the specified pixel value range, the conversion in accordance with the LUT may be regarded as a conversion which can reduce variation in pixel value in a region (e.g., the wiring pattern region or the background region) relatively (to a pixel value which is uncertain on which region it belongs to) or increase the difference of respective average values of the pixel values in the two regions (in other words, the approximate difference in pixel value between the two regions). As a result, it is possible to enhance the difference in pixel value between the regions in the enhanced differential image (or decrease of the difference of pixel values within one region or decrease of the difference of pixel values within one region while enhancing the difference in pixel value between the regions).

As shown in FIG. 7, by obtaining a threshold value for region division in a non-parametric manner from the reference image (or from the inspection image as discussed later), it is possible to appropriately perform a defect detection even if the difference in pixel value between a defect and a non-defect is small (or the contrast of image is small).

Figure 8:
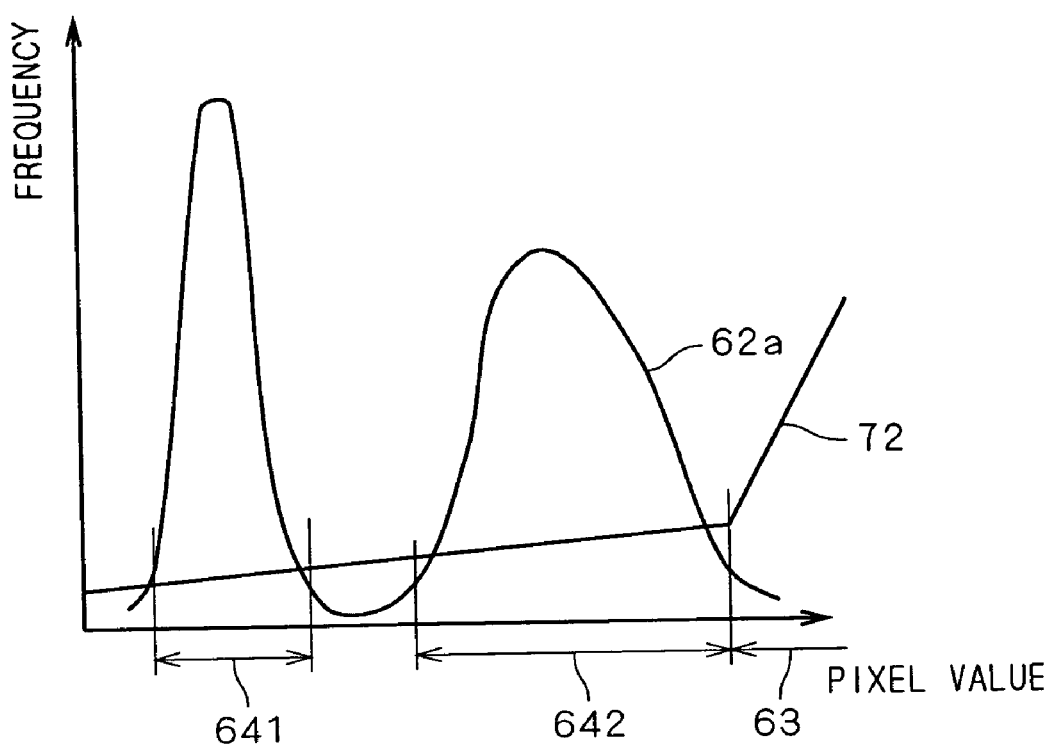

FIG. 8 is a graph illustrating another exemplary specified pixel value range. FIG. 8 shows a state where a range of pixel values which is larger than the pixel value range in which there are frequencies to some degrees is set as the specified pixel value range 63. When the reference image has two kinds of regions (for example, a wiring pattern region and the other background region on the substrate 9), a range of pixel values which is larger than each of the pixel value ranges 641 and 642 obtained from these regions is set as the specified pixel value range 63. Also in this case, the specified pixel value range 63 may be set manually by the user or automatically on the basis of the average values or the standard deviations of the peaks.

Then, as indicated by reference sign 72, a transfer curve (i.e., the LUT 61) enhancing the difference of any two pixel values in the specified pixel value range 63 is obtained. According to the transfer curve 72, when a pixel value which is extremely larger than the normal pixel value is found in the inspection image at a certain position, the pixel value at this position is enhanced in the enhanced differential image and easily detected as a defect. For example, in a case where the illumination light is abnormally reflected due to a foreign material defect having a specific reflectance on the substrate 9 and the pixel value in the inspection image becomes larger, it is possible to easily detect a defect.

It is preferable that the range 642 should be set large for the purpose of detecting a defect that a pixel value becomes extremely large. For example, a range consisting of pixel values equal to or more than a specified value obtained by adding three times the standard deviation a corresponding to the peak on the right side to an average value near the peak may be set as the specified pixel value range 63. By using the standard deviation, it is possible to appropriately obtain the pixel value range 642 corresponding to a specific region (such as the wiring pattern region) and position the specified pixel value range 63 outside the pixel value range 642 easily (in other words, on the basis of a certain criteria).

Thus, the specified pixel value range is set as a range of pixel values in the inspection image (or the reference image) where a defect is to be detected. By setting the specified pixel value range in accordance with the type of defect to be detected, it is possible to achieve detection of various defects with high precision.

Figure 9:
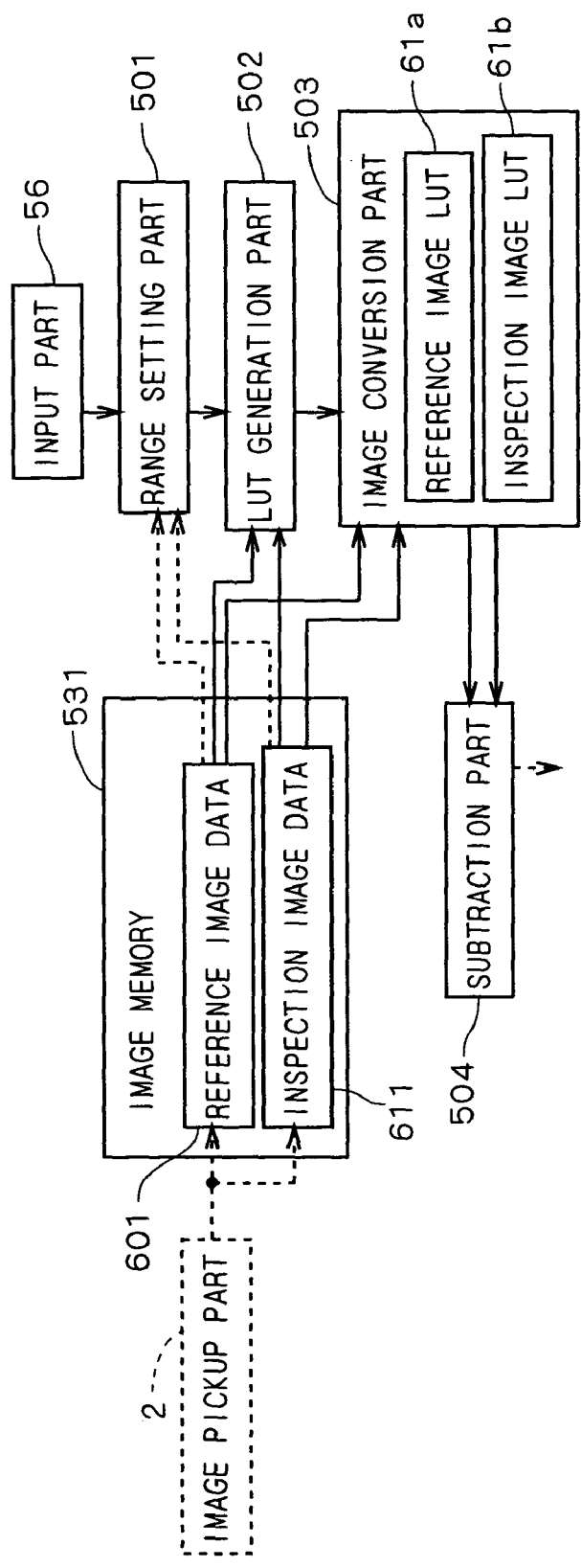
FIG. 9 is a diagram showing another exemplary functional structure of the computer.
Figure 10:
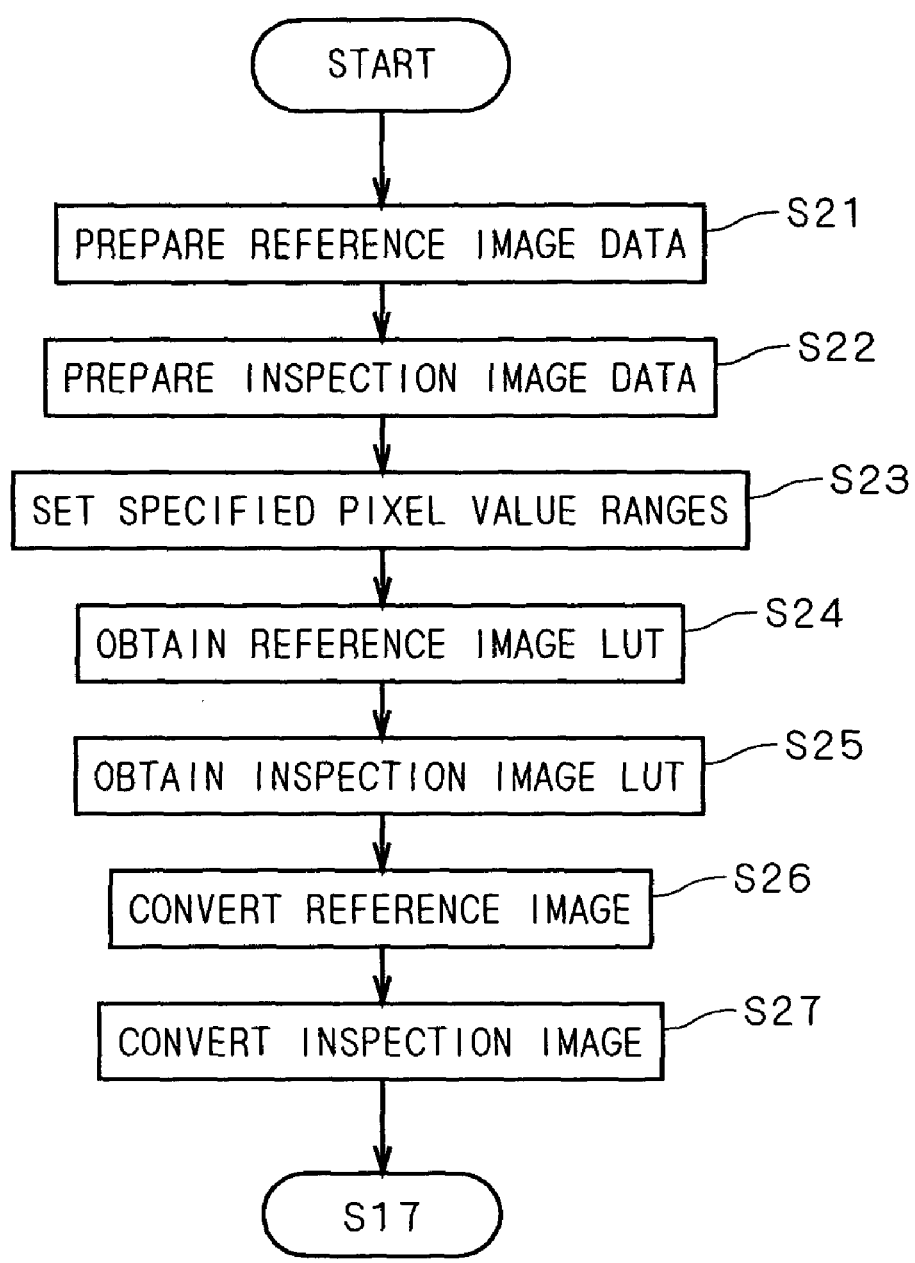
FIG. 10 is a flowchart showing another operation flow of the inspection apparatus.

FIG. 9 is a diagram showing another exemplary functions performed by an operation of the computer 5 in accordance with the program 80. The functional structure lower than the subtraction part 504 is the same as that of FIG. 4 and the functions identical to those of FIG. 4 are represented by the same reference signs. FIG. 10 is a flowchart showing the operation flow of the computer 5 shown in FIG. 9.

In the inspection apparatus 1 having the computer 5 of FIG. 9, first, an image of a predetermined region of one block on the substrate 9 is picked up by the image pickup part 2 and the reference image data 601 is stored in the image memory 531 (Step S21). Subsequently, the substrate 9 is moved and an image of a predetermined region of another block on the substrate 9 is picked up and inspection image data 611 is stored in the image memory 531 (Step S22).

In the range setting part 501, histograms of the reference image and the inspection image are obtained and a specified pixel value range for the reference image is set on the basis of the histogram of the reference image and a specified pixel value range for the inspection image is set on the basis of the histogram of the inspection image (Step S23). The specified pixel value ranges may be set manually or automatically. Automatic settings of the specified pixel value ranges for the inspection image and the reference image use the same method (i.e., algorithm).

Next, the LUT generation part 502 generates a reference image LUT 61*a* on the basis of the reference image data 601 (Step S24) and generates an inspection image LUT 61*b* on the basis of the inspection image data 611 (Step S25). Then, two generated LUTs 61*a* and 61*b* are stored in the image conversion part 503. A method of obtaining the inspection image LUT 61*b* is the same as the method of obtaining the reference image LUT 61*a* from the reference image and the specified pixel value range for reference image (for example, the method shown in FIGS. 6 to 8), except that the inspection image LUT 61*b* is generated on the basis of the specified pixel value range for inspection image and the histogram of the inspection image.

In the image conversion part 503, values of pixels in the reference image are transferred in accordance with the reference image LUT 61*a* (Step S26) and values of the corresponding pixels in the inspection image are transferred in accordance with the inspection image LUT 61*b* (Step S27). Thus, the converted reference image and the converted inspection image can be substantially obtained.

Both the pixels after transfer are inputted to the subtraction part 504, where a differential absolute value is obtained (Step S17 of FIG. 5), and the differential absolute value is compared with a predetermined threshold value by the comparison part 505 (Step S18) to acquire an inspection result for each pixel. Specifically, the differential absolute value image between the converted reference image and the converted inspection image is substantially obtained as an enhanced differential image, and further binarized by the predetermined threshold value. The inspection result, i.e., the binary image indicating defective pixels is stored in the memory 532 as the inspection result data 603 and displayed on the display 55 if necessary (Step S19).

Thus, in the computer 5 of FIG. 9, the LUTs which are used to convert the images are obtained for the reference image and the inspection image. This makes it possible to reduce an effect due to difference in quality of these images even if the reference image and the inspection image have different quality of image (e.g., brightness or distribution range of pixel values or the like).

For example, even if the histograms of the reference image and the inspection image each have bi-modality as shown in FIG. 6 and the positions of the peaks are deviated in these histograms, since each specified pixel value range is set with reference to the valley between the peaks, such a conversion as to relatively enhance the difference between any two pixel values in the valley in each image is performed. As a result, in each of the reference image and the inspection image, the pixel value of the enhanced differential image is appropriately enhanced relatively to a pixel which is hard to decide the specific region (for example, a wiring pattern or a background region on the substrate 9) it belongs to.

With the operation of FIG. 10, even if the histogram has one peak, it is possible to suppress an effect due to deviation between the position of the peak in the histogram of the reference image and that in the histogram of the inspection image.

Figure 11:
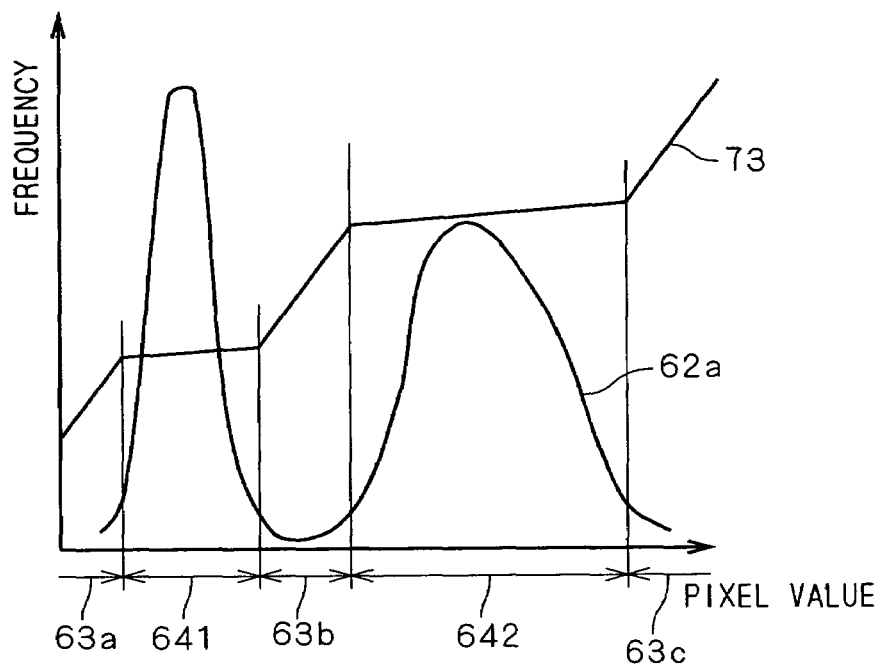
FIGS. 11 and 12 are graphs illustrating histograms and transfer curves.

FIG. 11 is a graph illustrating another example for setting the specified pixel value range and the transfer characteristics (LUT) on the basis of the histogram in the inspection apparatus 1. The histogram 62*a* of FIG. 11 has two peaks like that of FIG. 6 and the pixel value ranges 641 and 642 in two regions on the substrate 9, which correspond to these peaks, are obtained. Then, pixel value ranges other than the pixel value ranges 641 and 642 are set as specified pixel value ranges 63*a*, 63*b* and 63*c*.

Therefore, a transfer curve 73 which corresponds to the LUT has inclination which becomes larger in three specified pixel value ranges 63*a*, 63*b* and 63*c* and becomes smaller in the two pixel value ranges 641 and 642. As a result, a value of a pixel in the enhanced differential image which corresponds to the pixel belonging to one of the three specified pixel value ranges in the reference image and (or) the inspection image is enhanced. In other words, all the pixels each of which is uncertain on whether it belongs to a specific region on the substrate 9 or not are enhanced in the enhanced differential image.

Figure 12:
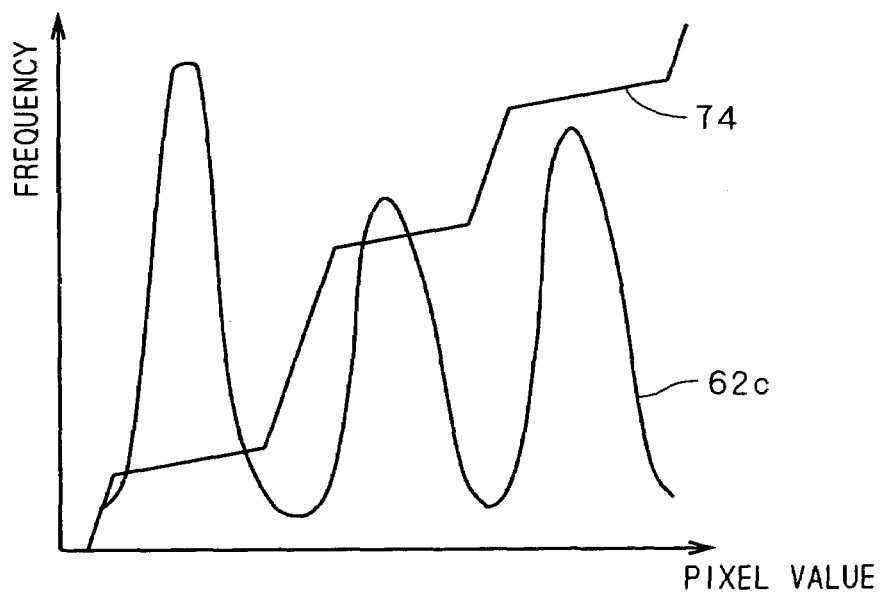
Figure 13:
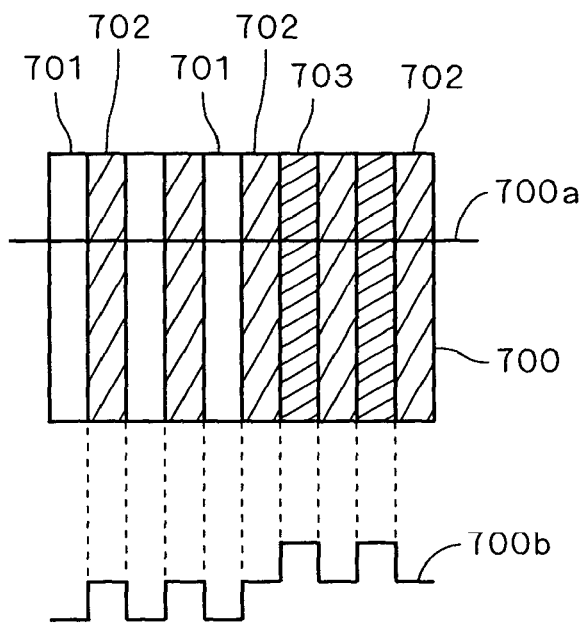
FIG. 13 is a view illustrating a reference image.

FIG. 12 is a graph illustrating the transfer curve 74 in a case where there are three (kinds of) regions on the substrate 9 and a histogram 62*c* having three peaks is obtained. For example, as shown in FIG. 13, when a reference image (or inspection image) 700 has a background region 701, a first wiring region 702 and a second wiring region 703 and pixel values on a line 700*a* are shown as a graph 700*b*, the histogram 62*c* illustrated in FIG. 12 is obtained.

A method of generating the transfer curve 74 of FIG. 12 is the same as that of FIG. 11, and the inclination of the transfer curve 74 is small in the pixel value ranges corresponding to the regions, pixel value ranges which do not correspond to these regions (including an extremely dark portion and an extremely bright portion) is set as the specified pixel value ranges, and the inclination of the transfer curve 74 is large in the specified pixel value ranges. When it is clear that the pixel values of a defect to be detected are present only in the specified pixel value range, it is not necessary to set many specified pixel value ranges as shown in FIG. 12.

Figure 14:
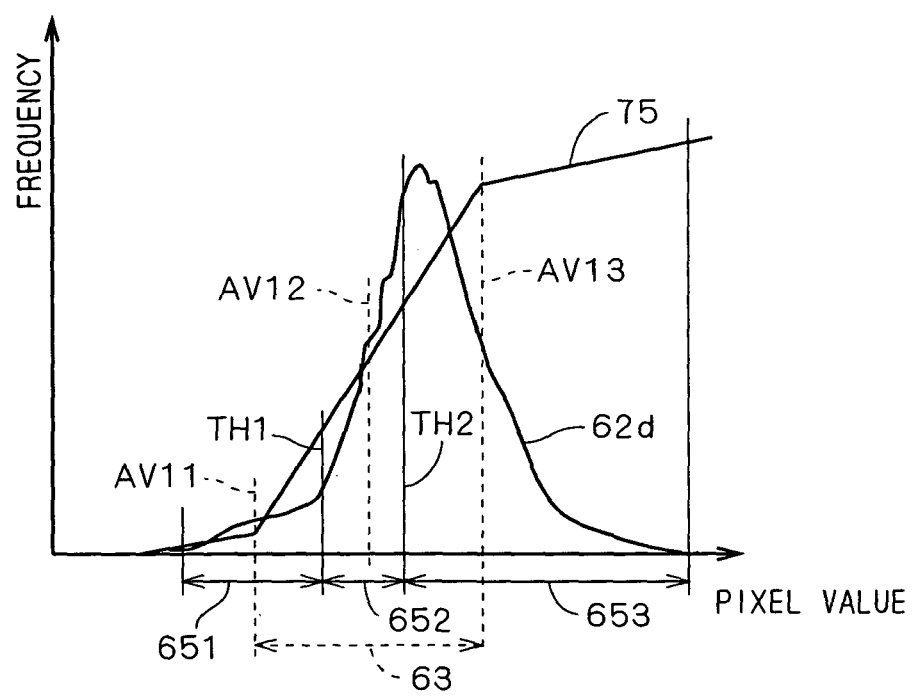
FIG. 14 is a graph illustrating a histogram and a transfer curve.

FIG. 14 is a graph illustrating setting of a specified pixel value range in a case where it is known in advance that there are three regions on the substrate 9 and a histogram 62*d* does not have peaks corresponding to these three regions.

When the histogram 62*d* of FIG. 14 is obtained, first, by using the method proposed in the above-mentioned document by Nobuyuki Otsu, two threshold values TH1 and TH2 for dividing the histogram 62*d* into three parts are obtained. Then, average values AV11, AV12 and AV13 of the three divided portions in the histogram 62*d* are obtained. Further, a range between the average value AV11 and the average value AV13 is set as the specified pixel value range 63 and the transfer curve 74 is obtained.

In the histogram 62*d*, the pixel value range 651 from a predetermined pixel value to the threshold value TH1, the pixel value range 652 from the threshold value TH1 to the threshold value TH2 and a pixel value range 653 from the threshold value TH2 to a predetermined pixel value are regarded as the specific regions on the substrate 9. When the pixel value ranges corresponding to these regions are not clear like in the histogram 62*d*, however, there arises a necessity of detecting a defect with emphasis on the pixel value range 652. Then, a range from the average value AV11 to the average value AV13, as a range including the pixel value range 652, is set as the specified pixel value range 63 and the transfer curve 75 having a large inclination in this pixel value range is set.

As a method of setting the threshold values in the case where peaks corresponding to those regions on the substrate 9 are not clearly present in the histogram, any other method may be used. Four or more kinds of regions may be present on the substrate 9 and it is not always necessary to know the number of kinds of regions in advance.

Figure 15:
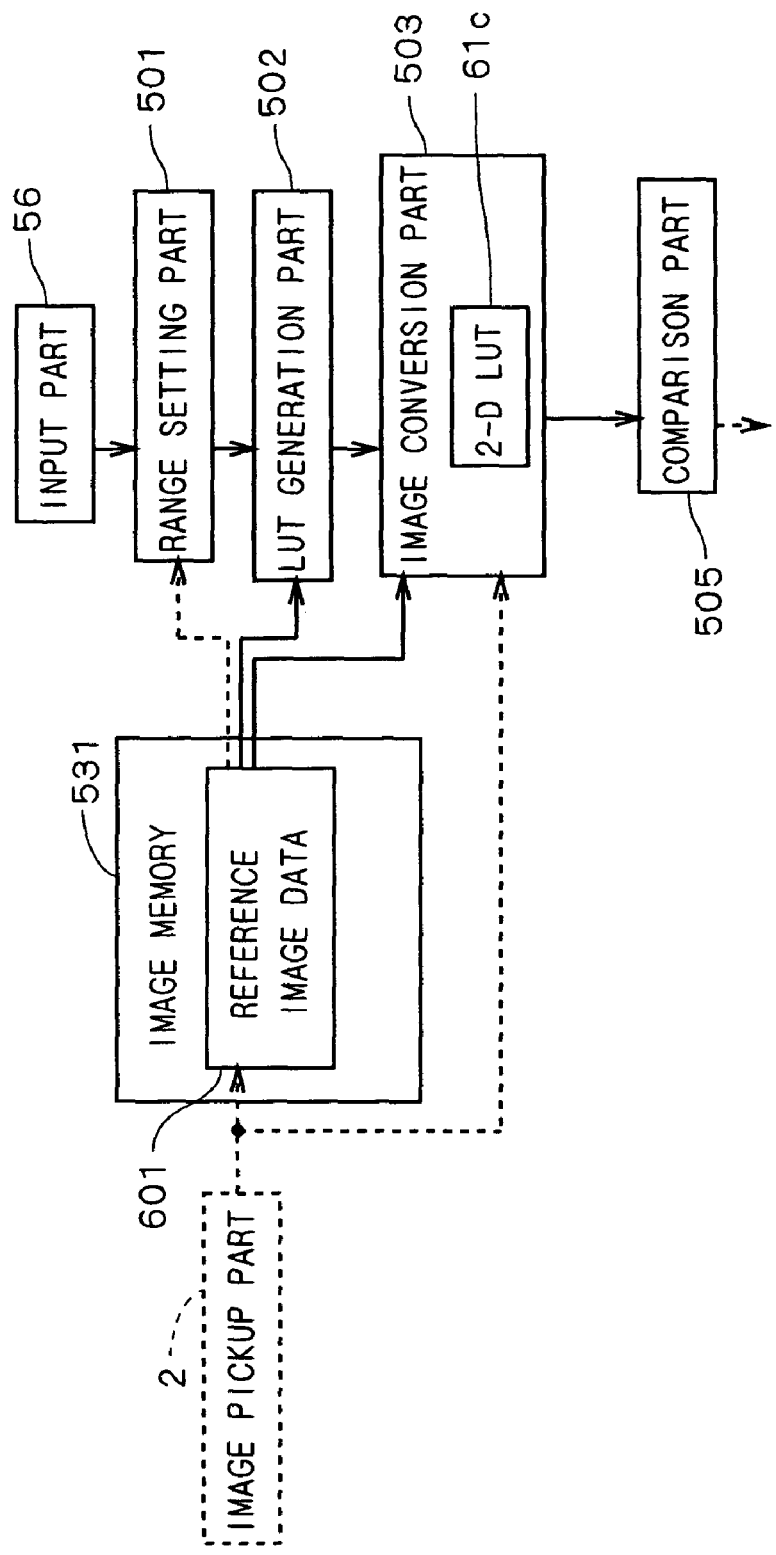
FIG. 15 is a diagram showing another exemplary functional structure of the computer.
Figure 16:
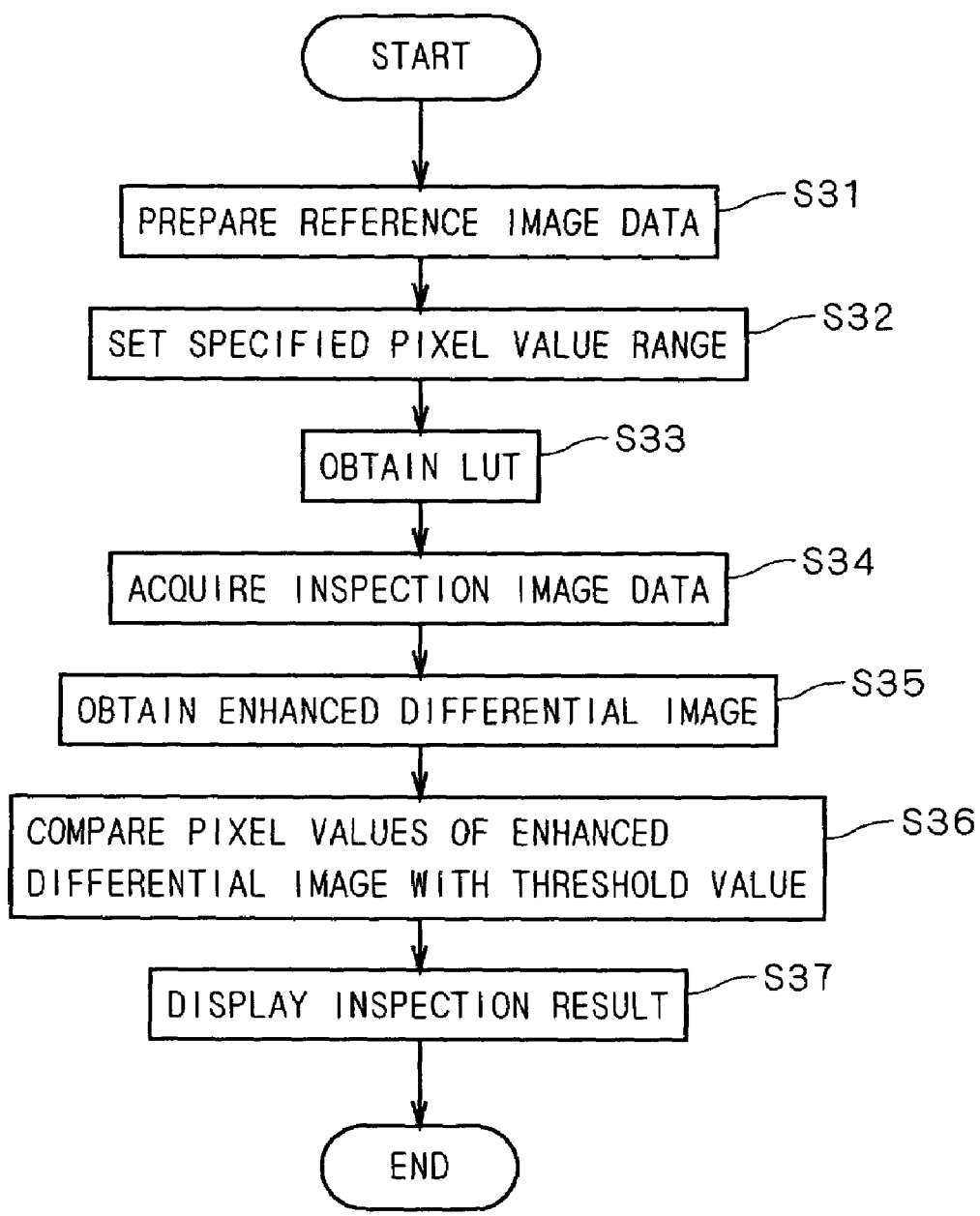
FIG. 16 is a flowchart showing an operation flow of the inspection apparatus.

FIG. 15 is a diagram showing still another exemplary functions performed by an operation of the computer 5 in accordance with the program 80. In FIG. 15, the subtraction part 504 is omitted from the structure of FIG. 4 and with the functional structure of FIG. 15, the enhanced differential image is generated without generating the converted reference image data 602. The functional structure lower than the comparison part 505 is the same as that of FIG. 4, and the functions identical to those of FIG. 4 are represented by the same reference signs. FIG. 16 is a flowchart showing the operation flow of the computer 5 of FIG. 15.

In the inspection apparatus 1 having the computer 5 of FIG. 15, first, the reference image data 601 is acquired by the image pickup part 2 and stored in the image memory 531 (Step S31), and the range setting part 501 performs setting of the specified pixel value range on the basis of the histogram of the reference image (Step S32).

Next, the LUT generation part 502 generates a 2-D (two-dimensional) LUT 61c on the basis of the reference image data 601 (Step S33) and the 2-D LUT 61c is stored in the image conversion part 503. The 2-D LUT 61c is a table whose inputs are a pixel value of the reference image and a value of the corresponding pixel of the inspection image, indicating the transfer characteristics for determining a pixel value of an enhanced differential image corresponding to the two inputs. Then, in the inspection apparatus 1, when the image pickup part 2 acquires the inspection image data (Step S34), the image conversion part 503 obtains each of pixel values of the enhanced differential image (Step S35) and the comparison part 505 compares the pixel value of the enhanced differential image with the threshold value, to thereby perform an inspection (Step S36). A comparison result is displayed on the display 55 if necessary (Step S37).

Figure 17A:
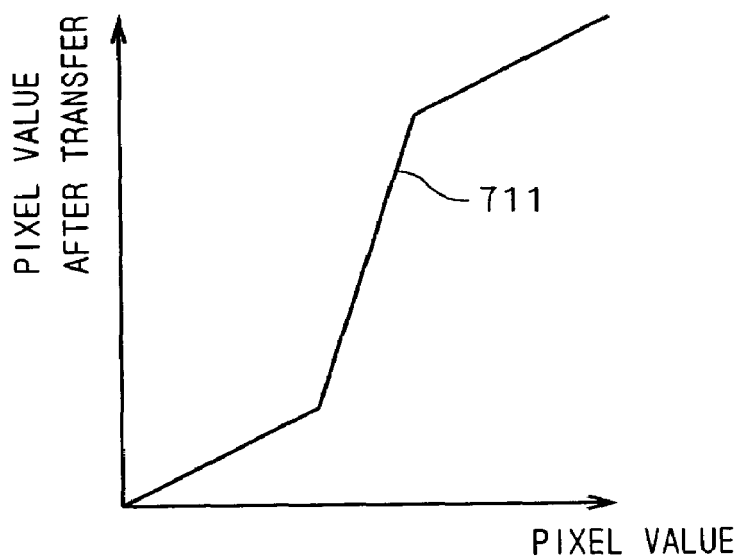
FIG. 17A is a graph illustrating a transfer curve.
Figure 17B:
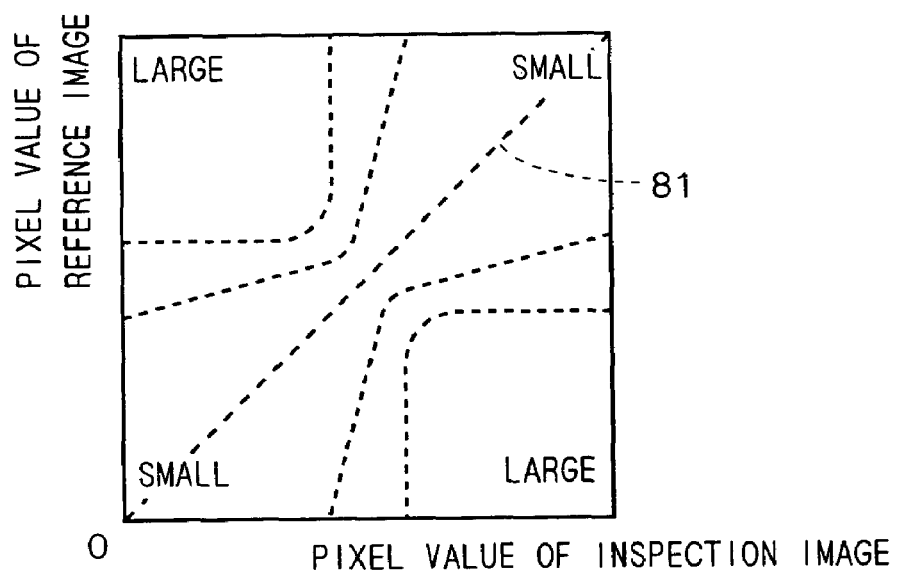
FIG. 17B is a view showing a 2-D (two-dimensional) LUT.

FIGS. 17A and 17B are views showing characteristics of an example of the 2-D LUT 61c generated by the LUT generation part 502, FIG. 17A shows a transfer curve (transfer characteristics) 711 in a case where it is supposed that the converted reference image (and the converted inspection image) should be generated, like in FIG. 4, and FIG. 17B schematically shows a state of the 2-D LUT 61c for generating the enhanced differential image in accordance with the transfer curve 711 of FIG. 17A. In FIG. 17B, the lower left is the origin (0, 0), and the horizontal axis indicates the pixel values of the inspection image and the vertical axis indicates the pixel values of the reference image. Then, a value of the table in a coordinate determined by these pixel values is specified as a pixel value of the enhanced differential image. The broken lines of FIG. 17B indicate magnitude of values included in the 2-D LUT 61c as contour lines.

Figure 18A:
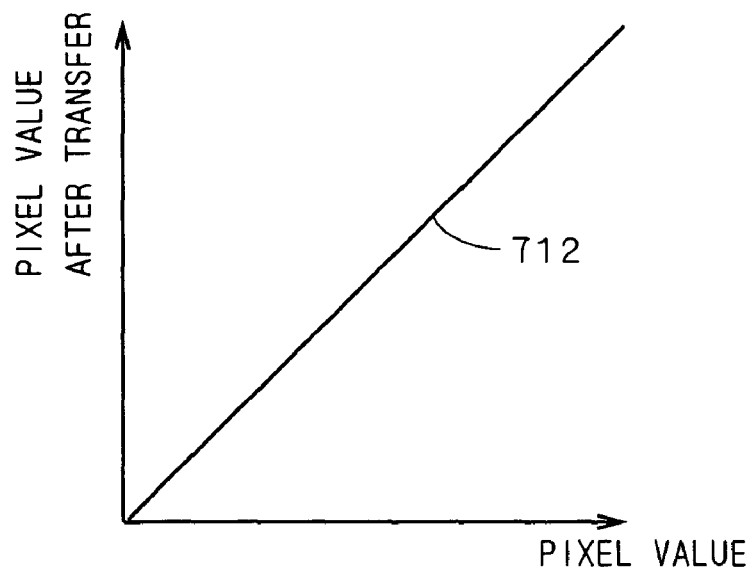
FIG. 18A is a graph illustrating a transfer curve without conversion (i.e., straight line)
Figure 18B:
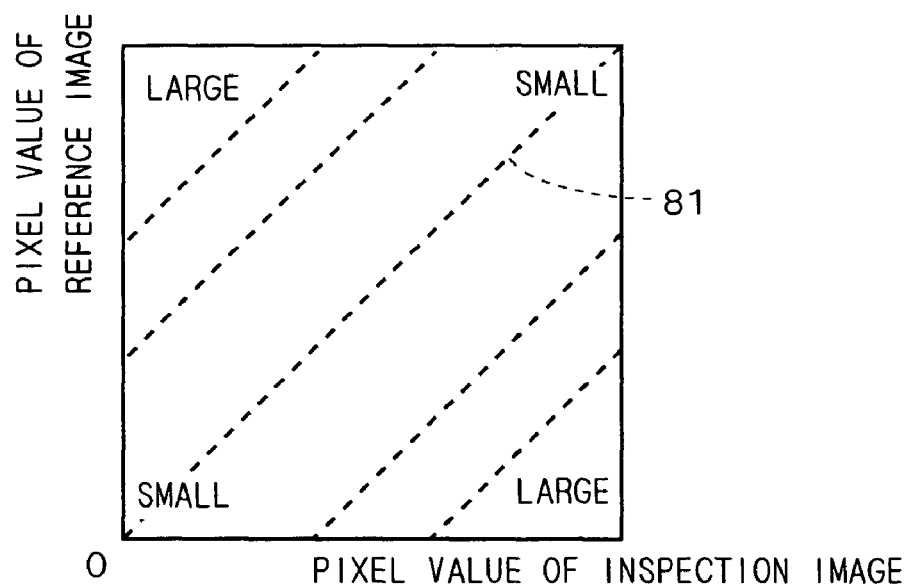
FIG. 18B is a view showing a 2-D LUT without enhancement of differential image.

FIGS. 18A and 18B are views showing characteristics of a 2-D LUT illustrated for reference. FIG. 18A shows a transfer curve 712 without transfer of pixel values (i.e., straight line), and FIG. 18B schematically shows the 2-D LUT corresponding to the transfer curve 712 of FIG. 18A. In the 2-D LUT of FIG. 18B, values in the 2-D LUT are in proportion to the distance from a diagonal line 81 so that the difference between the pixel value of the inspection image and the pixel value of the reference image should be an output value.

On the other hand, in the 2-D LUT 61c of FIG. 17B, a value "0" is stored on the diagonal line 81 but values in coordinates are set so that the contour lines protrude towards the center. As a result, when both the pixel value of the inspection image and the pixel value of the reference image belong to a pixel value range of the FIG. 17A which has a sharp inclination (i.e., in the neighborhood of the center of FIG. 17B), a relatively larger value than the difference between the pixel value of the inspection image and the pixel value of the reference image is specified in accordance with the 2-D LUT 61c. In contrast to this, when both the pixel value of the inspection image and the pixel value of the reference image belong to a pixel value range of the FIG. 17A which has a gentle inclination (i.e., on a side of the origin or the opposite side of the origin in FIG. 17A), a relatively smaller value than the difference between the pixel value of the inspection image and the pixel value of the reference image is specified in accordance with the 2-D LUT 61c.

Thus, the 2-D LUT 61c generated by the LUT generation part 502 is a table for obtaining the pixel value of the enhanced differential image directly and efficiently from the pixel value of the inspection image and the pixel value of the reference image without conversion of the reference image and the inspection image in accordance with the transfer characteristics. It is thereby possible to perform inspection in the inspection apparatus 1 at a high speed.

Figure 19:
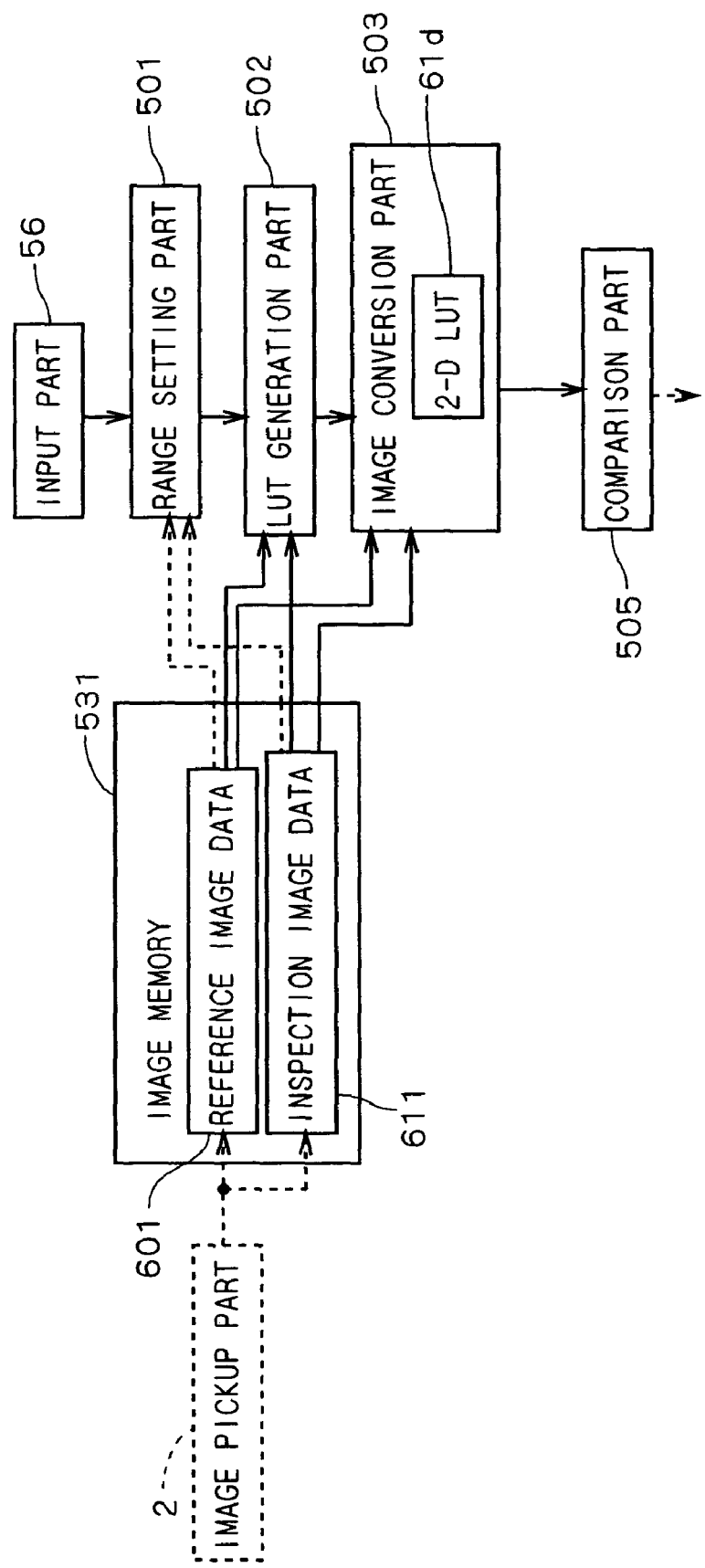
FIG. 19 is a diagram showing another exemplary functional structure of the computer.

FIG. 19 is a diagram showing another exemplary functional structure of the computer 5 in a case where the same operation as that for generating the enhanced differential image by using the reference image LUT 61a and the inspection image LUT 61b of FIG. 9 is performed by using the 2-D LUT. The functional structure of FIG. 19 is different from that of FIG. 9 in only that the subtraction part 504 is omitted and a 2-D LUT 61d is provided in the image conversion part 503.

In an operation of the computer 5 of FIG. 19, the same operations as those of Steps S21 to S23 of FIG. 10 are first performed and after that, the same operations as those of Steps S33 and S35 to S37 of FIG. 16 are performed. Specifically, the reference image data 601 and the inspection image data 611 are prepared in the image memory 531 (Steps S21 and S22) and the range setting part 501 sets the specified pixel value ranges on the basis of the histograms of these pixel values (Step S23). Then, the LUT generation part 502 generates the 2-D LUT 61d on the basis of the specified pixel value ranges (Step S33).

Figure 20A:
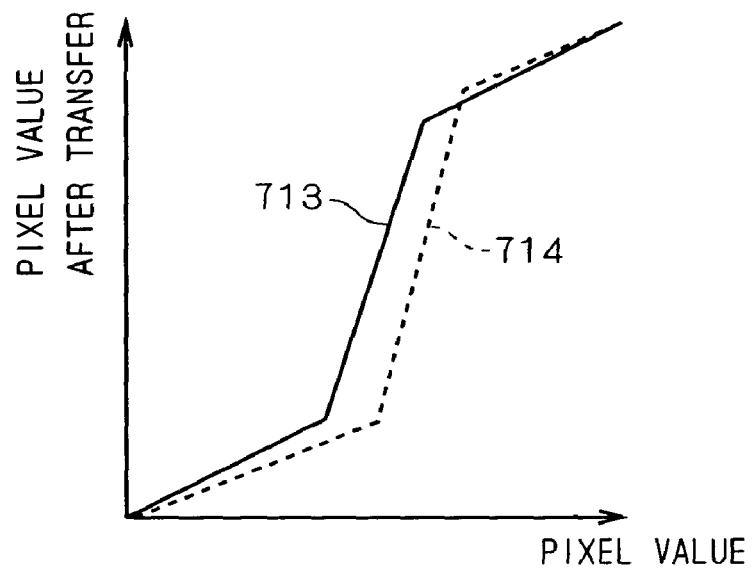
FIG. 20A is a graph illustrating transfer curves.
Figure 20B:
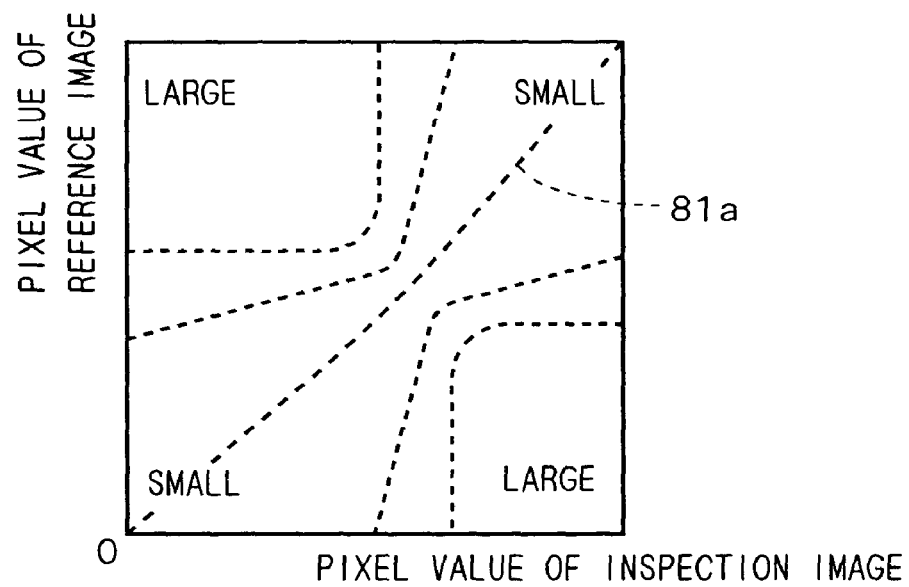
FIG. 20B is a view showing a 2-D LUT.

FIGS. 20A and 20B are views showing characteristics of an example of the 2-D LUT 61d. In FIG. 20A, a transfer curve 713 shows transfer characteristics derived from the reference image and a transfer curve 714 shows transfer characteristics derived from the inspection image. Correspondingly to these transfer characteristics, the 2-D LUT 61d of FIG. 20B are generated by the LUT generation part 502. The LUT generation part 502 may directly generate the 2-D LUT 61d from the specified pixel value ranges set for the reference image and the inspection image without obtaining the transfer curves of FIG. 20A.

In the 2-D LUT 61d of FIG. 20B, a value "0" is set approximately on a curve 81a and the contour lines are distorted as compared with those of the 2-D LUT 61c of FIG. 17B. This makes it possible to generate the enhanced differential image while reducing an effect due to difference in quality of these images even if the reference image and the inspection image have different quality of image (e.g., brightness or distribution range of pixel values), and therefore the same inspection as that by the structure of FIG. 9 can be performed at a high speed (see Steps S35 to 37).

Figure 21:
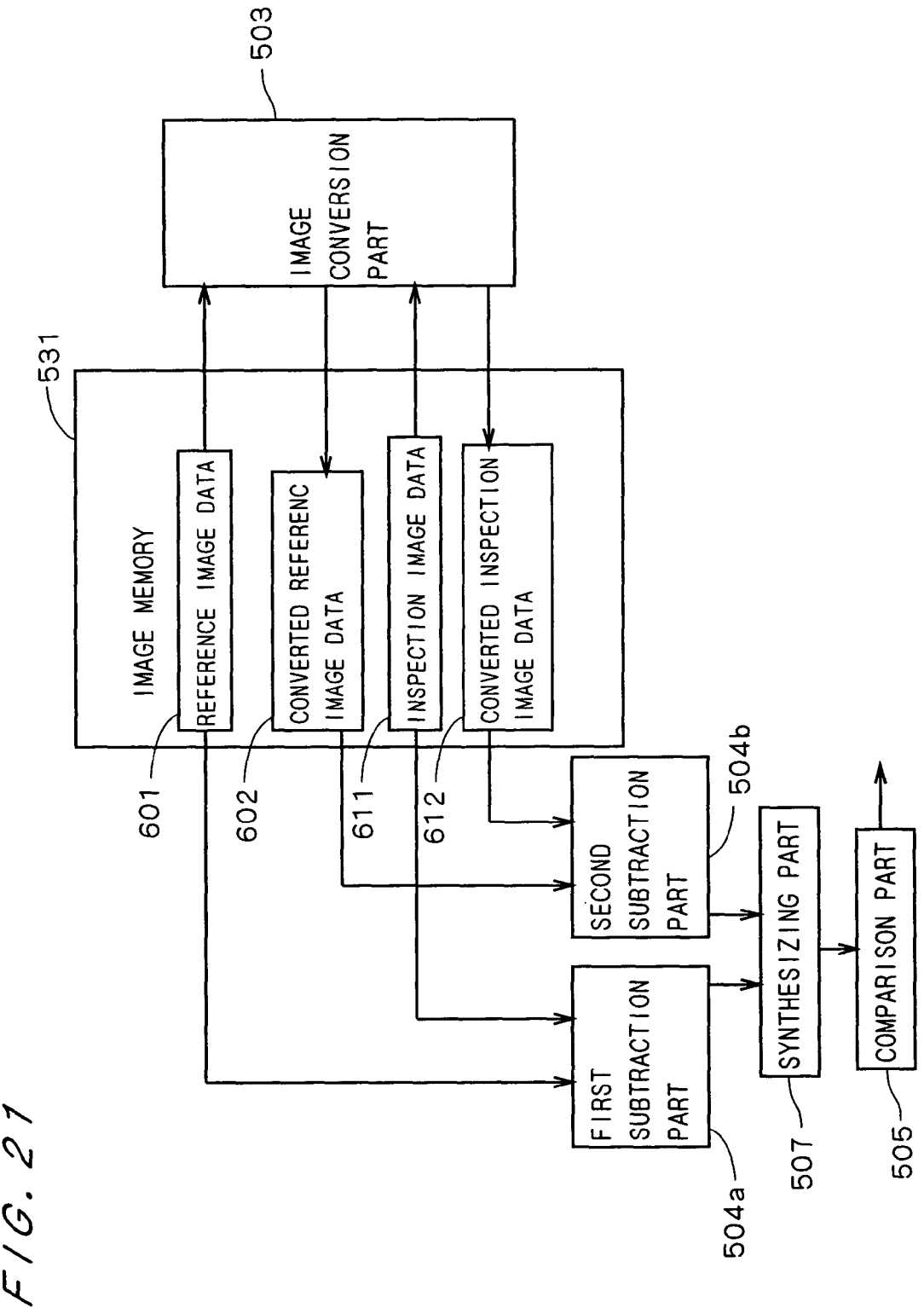
FIG. 21 is a diagram showing another exemplary functional structure of the computer.

Though appropriate inspection in accordance with the nature of defect is performed by obtaining the enhanced differential image in the preferred embodiment discussed above, the enhanced differential image may be processed by using the differential absolute value image (hereinafter, referred to as a "simple differential image") between the original reference image and the original inspection image. FIG. 21 is a diagram showing part of functional structure of the computer 5 in a case where the enhanced differential image and the simple differential image are synthesized in the structure of FIG. 4 or 9. In FIG. 21, the subtraction part 504 of the structure of FIG. 4 or 9 is replaced by a first subtraction part 504a, a second subtraction part 504b and a synthesizing part 507. Other constituent elements are identical to those of FIG. 4 or 9, and the elements are represented by the same reference signs in the following description.

Though FIG. 21 shows that the reference image data 601, the converted reference image data 602, the inspection image data 611 and the converted inspection image data 612 are stored in the image memory 531, there may be a case where the data other than the reference image data 601 are not stored in the image memory 531 but are inputted directly to the first subtraction part 504a and the second subtraction part 504b.

Figure 22:
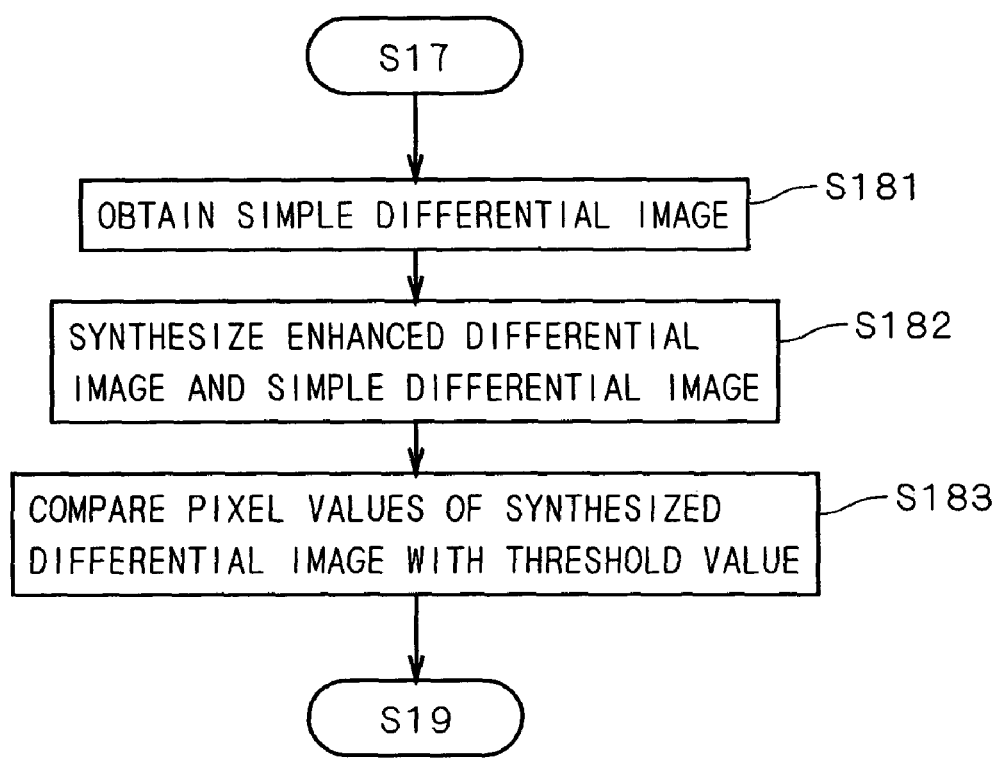
FIG. 22 is a flowchart showing part of an operation flow of the inspection apparatus.

When inspection is performed by the structure of FIG. 21, an operation of FIG. 22 is performed instead of Step S18 of FIG. 5. Also in the structure of FIG. 21, the LUT 61 of FIG. 4, the reference image LUT 61a and the inspection image LUT 61b of FIG. 9 are generated, the reference image data 601 and the inspection image data 611 are converted by the image conversion part 503 and the converted reference image data 602 and the converted inspection image data 612 are obtained (Steps S11 to S16 of FIG. 5, or Steps S21 to S27 of FIG. 10).

After that, these converted image data are inputted to the second subtraction part 504b and data of the enhanced differential image is generated (Step S17 of FIG. 5). At that time, the reference image data 601 and the inspection image data 611 are inputted to the first subtraction part 504a and data of the simple differential image is obtained (Step S181 of FIG. 22). Each pixel value of the enhanced differential image and the value of the corresponding pixel of the simple differential image are inputted to the synthesizing part 507 and the square root of (multiplication) product of these pixel values is obtained as a synthesized pixel value (Step S182). With this operation, data of a synthesized differential image which is obtained by substantially synthesizing the enhanced differential image and the simple differential image is generated.

Each of the pixel values in the synthesized differential image is compared with a predetermined threshold value by the comparison part 505 (Step S183), and the comparison result is stored in the memory 532 as the inspection result data 603 (see FIG. 4) and displayed on the display 55 if necessary (Step S19 of FIG. 5).

Thus, in the computer 5 comprising the structure of FIG. 21, detection of defective pixels is performed by synthesizing the enhanced differential image and the simple differential image and comparing the synthesized image with the predetermined threshold value. When a transfer curve(s) indicating the characteristics for converting the images is set through computation by the computer, it is preferable that the transfer curve should be bent as shown in FIGS. 6 to 8. In some cases, however, the enhancement of differential image is excessively performed by the bent line. Then, in such a case, the degree of enhancement is relieved by synthesizing the enhanced differential image and the simple differential image in the structure of FIG. 21, and appropriate inspection is thereby achieved.

Figure 23:
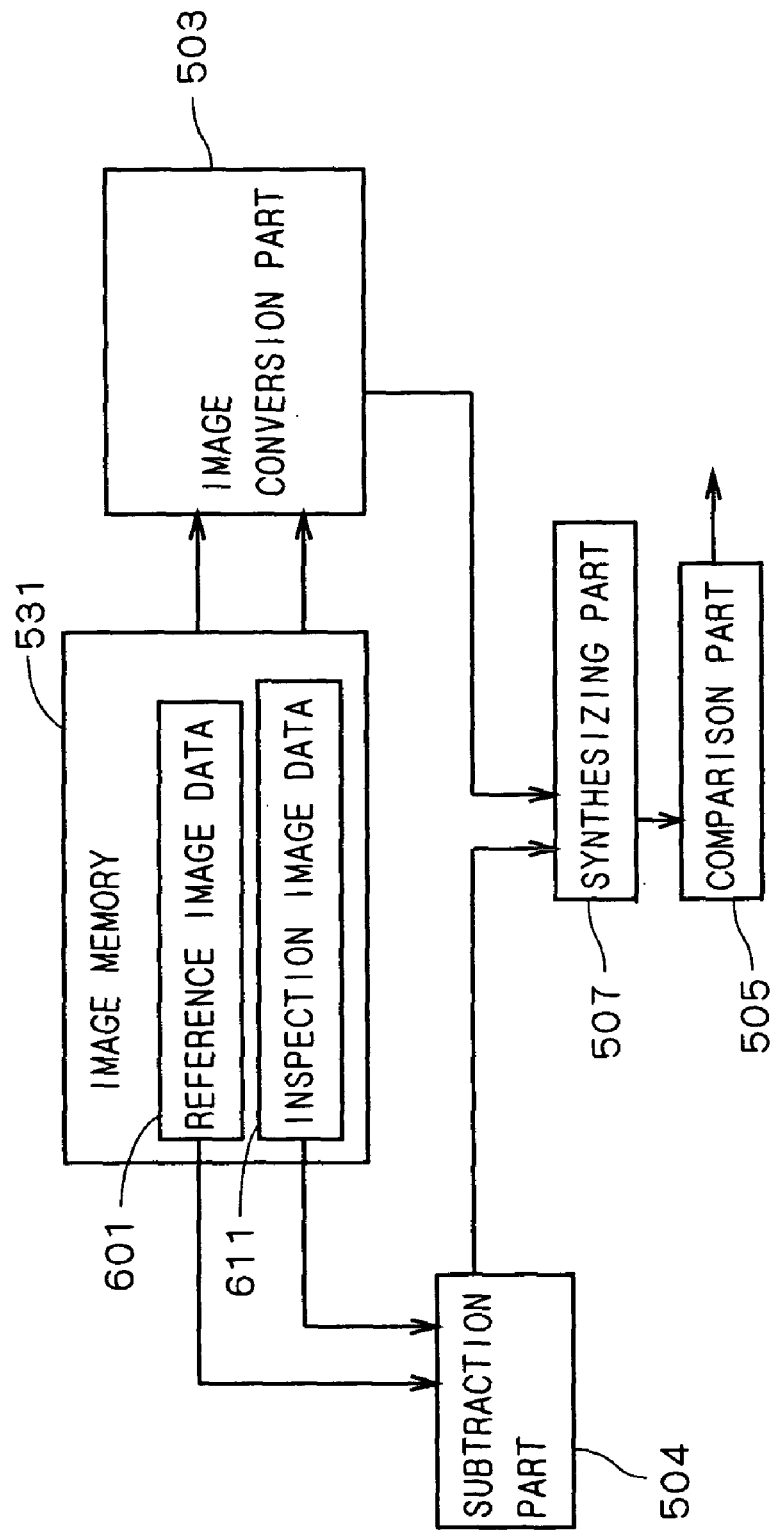
FIG. 23 is a diagram showing another exemplary functional structure of the computer.

FIG. 23 is a diagram showing a structure for synthesizing the enhanced differential image and the simple differential image in a case of using the 2-D LUT (see FIG. 15 or 19). In the structure of FIG. 23, a 2-D LUT is provided in the image conversion part 503, and an enhanced differential image is directly generated by the image conversion part 503 from the reference image data 601 and the inspection image data 611 and inputted to the synthesizing part 507. On the other hand, subtraction of the reference image data 601 and the inspection image data 611 is performed by the subtraction part 504 to generate data of a simple differential image and the data of simple differential image is inputted to the synthesizing part 507. Then, the enhanced differential image and the simple differential image are synthesized by the synthesizing part 507 and each pixel value of the synthesized differential image is compared with a predetermined threshold value by the comparison part 505, to perform an inspection. In other words, the same operation as that in the structure of FIG. 21 is performed, except that the data of enhanced differential image is directly generated by the image conversion part 503.

Figure 24:
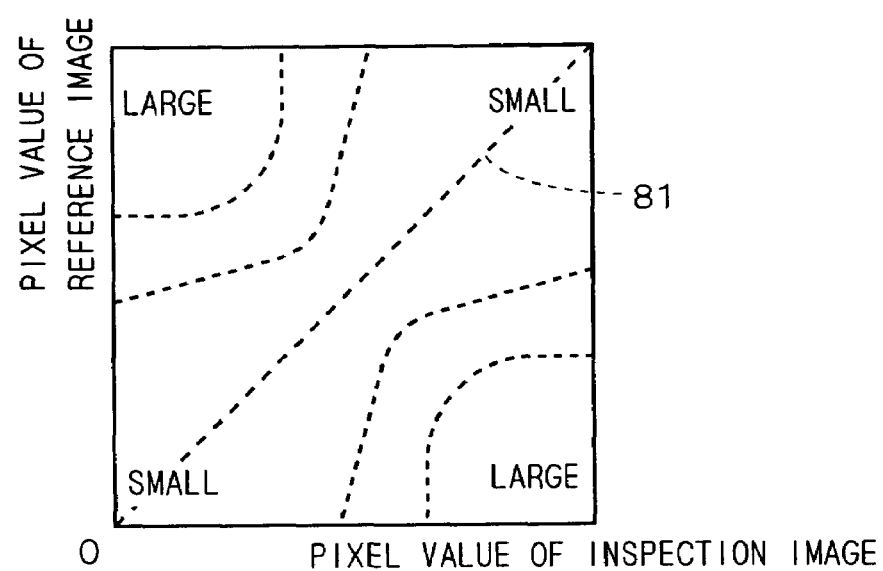
FIG. 24 is a view showing a 2-D LUT.
Figure 25A:
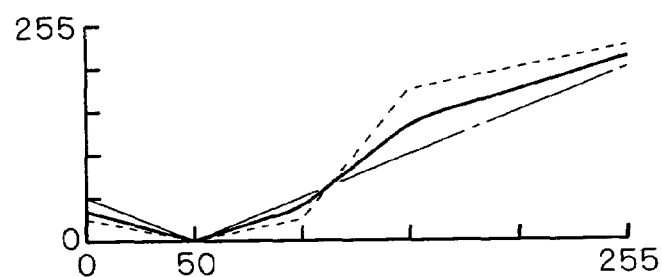
FIGS. 25A to 25D are graphs showing characteristics of the 2-D LUT.
Figure 25B:
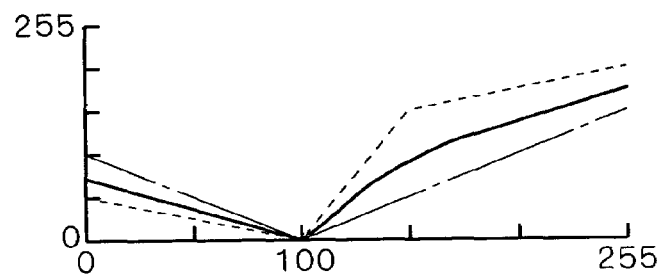
Figure 25C:
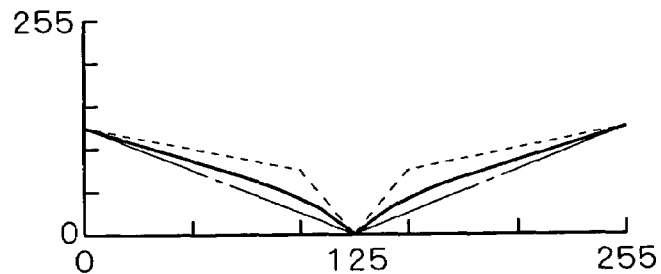
Figure 25D:
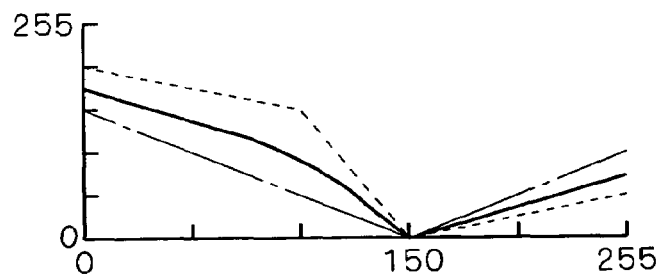

In the 2-D LUT of the image conversion part 503, values including the synthesizing operation may be stored. In this case, the structure of the inspection apparatus 1 is the same as that of FIG. 15 or 19. FIG. 24 is a view showing a 2-D LUT which is obtained by adding the synthesizing operation to the 2-D LUT of FIG. 17B. FIGS. 25A to 25D are graphs showing a relation between the pixel values of the reference image and values stored in the LUT (i.e., the pixel values of the synthesized differential image) in a case where the pixel values of the inspection image are 50, 100, 125 and 150, respectively.

As shown in FIG. 24, the 2-D LUT has a gentle change (i.e., distribution) of values in the LUT as compared with that of FIG. 17B. In FIGS. 25A to 25D, the solid line indicates a relation between the pixel values of the reference image and the values in the LUT of FIG. 24, the broken line indicates a relation between the pixel values of the reference image and the values in the LUT in FIG. 17B and the alternate long and short dash line indicates a relation between the pixel values of the reference image and the values in the LUT in FIG. 18B (in other words, the LUT in a case where enhancement of the differential absolute value image is not performed).

As shown in FIGS., 25A to 25D, in an image converted in accordance with the 2-D LUT of FIG. 24, the degree of enhancement of the enhanced differential image is relieved with the simple differential image. By directly generating the synthesized differential image with the 2-D LUT, it is possible to simplify the computation of the computer 5 in the inspection apparatus 1.

Figure 26:
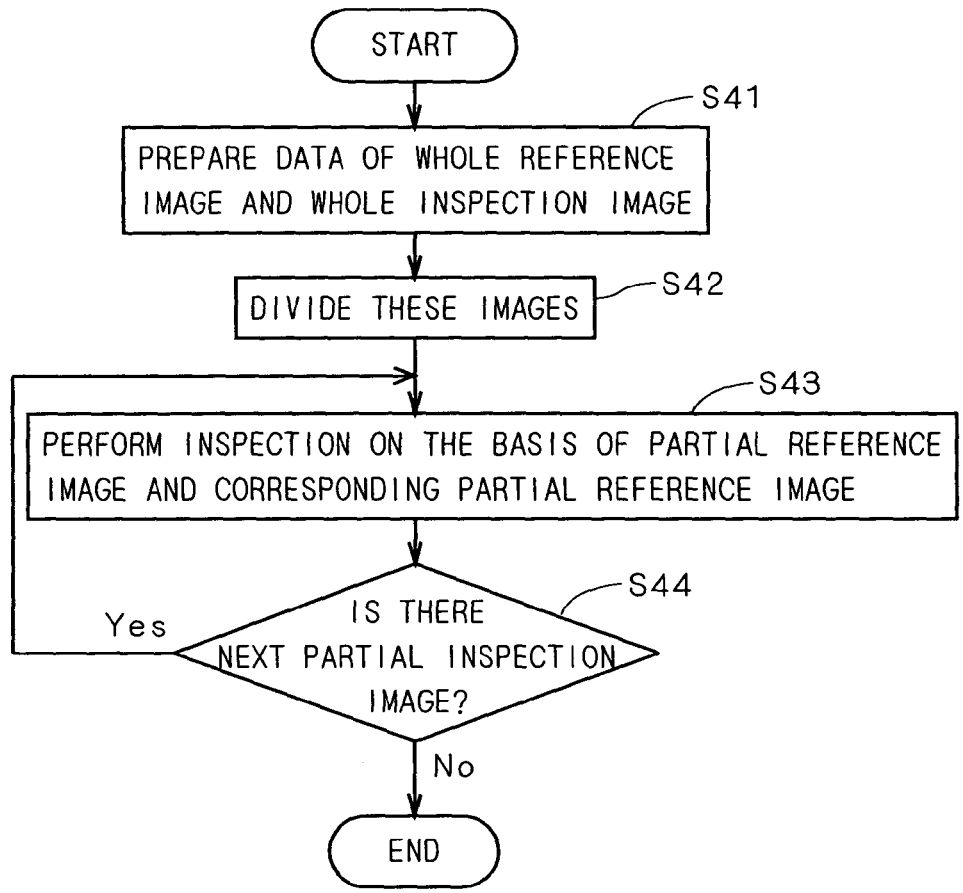
FIG. 26 is a flowchart showing an operation flow of the inspection apparatus.

In the inspection apparatus 1, though the whole reference image and the whole inspection image are compared in the above discussion, the inspection may be performed for part of the reference image and part of the inspection image. In other words, part of the image acquired by the image pickup part 2 may serve as the inspection image in the above discussion. Hereinafter, the image acquired by the image pickup part 2 is referred to as a whole inspection image and part of the whole inspection image to be computed is referred to as a partial inspection image. In accordance with this, the whole and part of the reference image are also referred to as a whole reference image and a partial reference image, respectively. FIG. 26 is a flowchart showing an operation flow of the inspection apparatus 1 in a case where inspection is performed partial inspection image.

Figure 27:
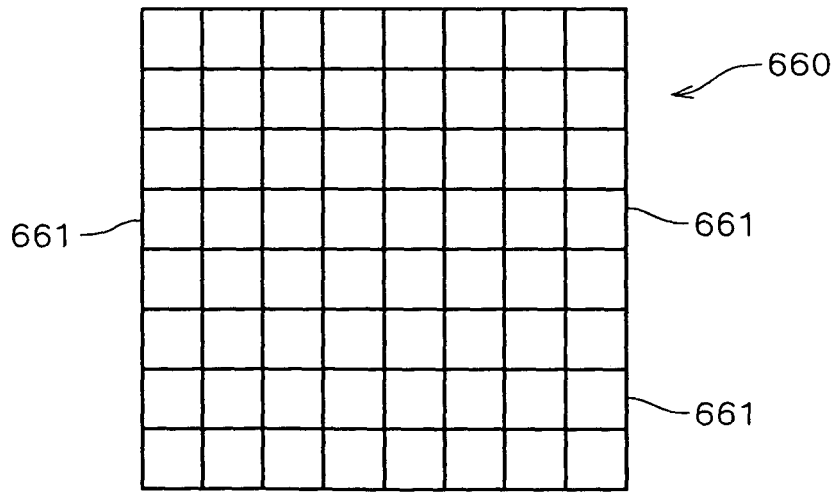
FIG. 27 is a view illustrating partial images.

First, when data of the whole reference image and the whole inspection image are acquired by the image pickup part 2 and prepared (Step S41), the whole reference image and the whole inspection image are divided into a plurality of partial reference images and partial inspection images (Step S42). FIG. 27 is a view illustrating division of an image 660 (the whole reference image or the whole inspection image) into a plurality of partial images 661. The above operation is performed for data of one partial reference image and data of one partial inspection image, an enhanced differential image or a synthesized differential image corresponding to the partial inspection image is obtained and each pixel in the enhanced differential image or the synthesized differential image is compared with a threshold value, to perform inspection (Step S43).

When the inspection for one partial inspection image is finished, inspection for the next partial inspection image is performed and when the inspection for all the partial inspection images are completed, the inspection for the whole inspection image is thereby finished (Step S44). By performing the inspection after dividing the whole inspection image (and the whole reference image), even if regions in the whole inspection image are different in quality of image from one another, appropriate inspection can be performed on the whole of inspection image.

Though the preferred embodiment of the present invention has been discussed above, the present invention is not limited to the above-discussed preferred embodiment, but allows various variations.

For example, the inspection image and the reference image may be part of an image acquired by the image pickup part 2. There may be a case, for example, where an image having repeating patterns is acquired by the image pickup part 2 and part of the image serves as a reference image and other part serves as an inspection image. Further, the reference image may be an average image of a plurality of images on the substrate 9 which correspond to one another or the reference image data may be generated in advance on the basis of a design data of pattern on the substrate 9.

Though the LUT(s) is generated on the basis of only the reference image or on the basis of the reference image and the inspection image in the above-discussed preferred embodiment, the LUT may be generated on the basis of only the pixel values of the inspection image. By obtaining the LUT on the basis of the reference image or the inspection image, the characteristics of the reference image or the inspection image can be reflected in the LUT and automatic generation of LUT can be achieved.

The transfer curve indicating the transfer characteristics in accordance with the LUT is not needed to be bent (i.e., lines) but may be a smooth curve only if such conversion as to enhance the difference between any two pixel values in the specified pixel value range can be performed.

Though the enhanced differential image is generated so that the difference of any (two) pixel values should be enhanced within the specified pixel value range which is specified in the defect detection in the above-discussed preferred embodiment, the specified pixel values may be discrete. In other words, there may be a case where only the difference between any pixel values among a plurality of specified pixel values is enhanced. This allows appropriate inspection with attention to the specified pixel values. The specified pixel value range in the above preferred embodiment can be regarded as a set of specified pixel values or a range including a plurality of specified pixel values.

It is not necessary that the whole range of pixel values of the converted image should be equal to the whole range of pixel values of the image before conversion in the structures of FIGS. 4, 9 and 21. There may be a case, for example, where the range of pixel values before conversion is from 0 to 255 and the range of pixel values after conversion is from 0 to 1 which are high-precision real numbers. Similarly, the range of pixel values in the enhanced differential image obtained by the image conversion part 503 in the structures of FIGS. 15, 19 and 23 may be from 0 to 1 which are high-precision real numbers. The threshold value which is compared with the enhanced differential image or the synthesized differential image is set as appropriate in accordance with the range of pixel values of the image. After transfer to the pixel values ranging from 0 to 1, the pixel values may be further transferred to those in the range from 0 to 255.

In FIGS. 21 and 23, as a method of synthesizing the enhanced differential image and the simple differential image, other methods may be used. A (multiplication) product of the pixel value of the enhanced differential image and the pixel value of the simple differential image may become an object to be compared in the comparison part 505, and synthesis may be performed by adding the pixel value of the enhanced differential image and the pixel value of the simple differential image at a constant ratio. As a specific example, the pixel value of the synthesized differential image may be obtained by synthesizing the pixel value of the enhanced differential image and the pixel value of the simple differential image with parameter t ($0<t<1$) (this parameter may be ($0 \leq t \leq 1$)) at the ratio of ($t:(1-t)$). In this case, by changing the parameter t, it is possible to easily change the degree of synthesis of the enhanced differential image and the simple differential image.

It is not necessary to perform the inspection on each pixel, and for example, a set of pixels (e.g., 2×2 pixels) may be handled as one pixel in the above preferred embodiment. In other words, the pixel in the above preferred embodiment is not needed to strictly correspond to a physical pixel which is a constituent of an image.

Though the image acquired by the image pickup part 2 is processed by the computer 5 in the above-discussed preferred embodiment, part of the functions shown in FIGS. 4, 9, 15, 19, 21 and 23 may use dedicated circuits for faster operation. Especially, the functions of the image conversion part 503, the subtraction part 504, the comparison part 505 and the like can be easily performed by dedicated circuits, and using dedicated circuits allows faster inspection after generation of the LUT(s).

The inspection apparatus 1 can be used not only for the inspection of pattern on a semiconductor substrate but also for inspection of fine patterns on various substrates, such as patterns formed on a color filter, a shadow mask, a high-definition printed circuit board or the like, pattern of lead frame, pattern of photomask used for forming these patterns or the like.

While the invention has been shown and described in detail, the foregoing description is in all aspects illustrative and not restrictive. It is therefore understood that numerous modifications and variations can be devised without departing from the scope of the invention.

What is claimed is:

1. A defect inspection apparatus for inspecting a pattern on an object, comprising:
    an image pickup device for performing an image pickup of an object to acquire data of an inspection image which is multitone;
    a memory for storing data of a reference image; and
    an operation part for performing the steps of:
        setting a specified pixel value range which is positioned between representative pixel values of two regions in said inspection images and/or said reference image, said two regions corresponding to two kinds of regions on said object;
        obtaining transfer characteristics to enhance a difference between arbitrary pixel values included in said specified pixel value range relative to a difference between arbitrary pixel values other than said specified pixel value range;

obtaining an enhanced differential image between said inspection image and said reference image on the basis of said transfer characteristics; and performing an inspection on the basis of said enhanced differential image.

2. The defect inspection apparatus according to claim 1, wherein said operation part converts said inspection image and said reference image on the basis of said transfer characteristics to obtain a differential image between a converted inspection image and a converted reference image as said enhanced differential image.

3. The defect inspection apparatus according to claim 1, wherein said representative pixel values are average values of values of pixels belonging to said two regions, respectively.

4. A defect inspection apparatus for inspecting a pattern on an object comprising:

an image pickup device for performing an image pickup of an object to acquire data of an inspection image which is multitone a memory for storing data of a reference image; and an operation part for performing the steps of:

setting a specified pixel value range which is positioned outside a pixel value range corresponding to a specific region in said inspection image and/or said reference image, said specific region corresponding to a specific kind of region on said object;

obtaining transfer characteristics to enhance a difference between arbitrary pixel values included in said specified pixel value range relative to a difference between arbitrary pixel values other than said specified pixel value range;

obtaining an enhanced differential image between said inspection image and said reference image on the basis of said transfer characteristics and performing an inspection on the basis of said enhanced differential image.

5. The defect inspection apparatus according to claim 4, wherein said pixel value range corresponding to said specific region is set on the basis of a standard deviation of values of pixels belonging to said specific region.

6. The defect inspection apparatus according to claim 1, wherein said transfer characteristics include inspection image transfer characteristics obtained from said inspection image and reference image transfer characteristics obtained from said reference image.

7. The defect inspection apparatus according to claim 1, wherein said operation part synthesizes a differential image between said inspection image and said reference image and said enhanced differential image and compares values of pixels in a synthesized image with a predetermined threshold value, to perform inspection.

8. The defect inspection apparatus according to claim 1, wherein each of a plurality of images which are obtained by dividing an image acquired by said image pickup part is said inspection image.

9. A defect inspection method for inspecting pattern on an object, comprising the steps of:

a) preparing data of a reference image;

b) performing an image pickup of an object to acquire data of an inspection image which is multitone;

c) setting a specified pixel value range which is positioned between representative pixel values of two regions in said inspection image and/or said reference image, said two regions corresponding to two kinds of regions on said object;

d) obtaining transfer characteristics to enhance difference between arbitrary pixel values included in said specified pixel value range relatively to difference between arbitrary pixel values other than said specified pixel value range;

e) obtaining an enhanced differential image between said inspection image and said reference image on the basis of said transfer characteristics; and f) performing inspection on the basis of said enhanced differential image.

10. The defect inspection method according to claim 9, wherein said inspection image and said reference image are converted on the basis of said transfer characteristics to obtain a differential image between a converted inspection image and a converted reference image as said enhanced differential image in said step e).

11. The defect inspection method according to claim 9, wherein said representative pixel values are average values of values of pixels belonging to said two regions, respectively.

12. A defect inspection method for inspecting a pattern on an object, comprising the steps of:

a) preparing data of a reference image b) performing an image pickup of an object to acquire data of an inspection image which is multitone;

c) setting a specified pixel value range which is positioned outside a pixel value range corresponding to a specific region in said inspection image and/or said reference image, said specific region corresponding to a specific kind of region on said object;

d) obtaining transfer characteristics to enhance a difference between arbitrary pixel values included in said specified pixel value range relative to a difference between arbitrary pixel values other than said specified pixel value range;

obtaining an enhanced differential image between said inspection image and said reference image on the basis of said transfer characteristics; and f) performing inspection on the basis of said enhanced differential image.

13. The defect inspection method according to claim 12, wherein said pixel value range corresponding to said specific region is set on the basis of a standard deviation of values of pixels belonging to said specific region.

14. The defect inspection method according to claim 9, wherein said transfer characteristics include inspection image transfer characteristics obtained from said inspection image and reference image transfer characteristics obtained from said reference image.

15. The defect inspection method according to claim 9, wherein said step f) comprises the steps of:

synthesizing a differential image between said inspection image and said reference image and said enhanced differential image; and comparing values of pixels in a synthesized image with a predetermined threshold value.

16. A computer-readable recording medium carrying a program for executing inspection of pattern, wherein execution of said program by a computer causes said computer to perform the steps of:
   a) preparing data of a reference image;
   b) preparing data of an inspection image which is multitone;
   c) setting a specified pixel value range which is positioned between representative pixel values of two regions in said inspection image and/or said reference image, said two regions corresponding to two kinds of regions on said object;
   d) obtaining transfer characteristics to enhance a difference between arbitrary pixel values included in said specified pixel value range relative to a difference between arbitrary pixel values other than said specified pixel value range;
   e) obtaining an enhanced differential image between said inspection image and said reference image on the basis of said transfer characteristics; and
   f) performing inspection on the basis of said enhanced differential image.

17. The defect inspection apparatus according to claim 1, wherein
said transfer characteristics are obtained in the form of two-dimensional lookup table, and said enhanced differential image is obtained by using said two-dimensional lookup table.

18. The defect inspection apparatus according to claim 4 wherein
said transfer characteristics include inspection image transfer characteristics from said inspection image and reference image transfer characteristics obtained from said reference image.

19. The defect inspection apparatus according to claim 4 wherein
said operation part synthesizes a differential image between said inspection image and said reference image and said enhanced differential image and compares values of pixels in a synthesized image with a predetermined threshold value, to perform inspection.

20. The defect inspection apparatus according to claim 4 wherein
each of a plurality of images which are obtained by dividing an image acquired by said image pickup part is said inspection image.

21. The defect inspection apparatus according to claim 4 wherein
said transfer characteristics are obtained in the form of a two-dimensional lookup table, and said enhanced differential image is obtained by using said two-dimensional lookup table.

22. The defect inspection method according to claim 9 wherein
said transfer characteristics are obtained in the form of a two-dimensional lookup table and said enhanced differential image is obtained by using said two-dimensional lookup table.

23. The defect inspection method according to claim 12 wherein
said transfer characteristics include inspection image transfer characteristics obtained from said inspection image and reference image transfer characteristics obtained from said reference image.

24. The defect inspection method according to claim 12 wherein
said step f) comprises the steps of:
synthesizing a differential image between said inspection image and said reference image and said reference image and enhanced differential image; and
comparing values of pixels in a synthesized image with a predetermined threshold value.

25. The defect inspection method according to claim, 12 wherein
said transfer characteristics are obtained in the form of a two-dimensional lookup table and said enhanced differential image is obtained by using said two-dimensional lookup table.

* * * * *